United States Patent
Saleh et al.

(10) Patent No.: US 9,650,374 B2
(45) Date of Patent: May 16, 2017

(54) PHOTOCHROMIC TETRAHYDROINDOLIZINES

(71) Applicant: UMM AL-QURA UNIVERSITY, Makkah (SA)

(72) Inventors: Saleh Abdel-Mgeed Ahmed Saleh, Makkah (SA); Mohamed Mokhtar Mohamed Abdalla, Benha (EG); Khalid Soliman Khalil Khairou, Makkah (SA)

(73) Assignee: Umm Al-Qura University, Makkan (SA)

( * ) Notice: Subject to any disclaimer, the term of this patent is extended or adjusted under 35 U.S.C. 154(b) by 202 days.

(21) Appl. No.: 14/400,656

(22) PCT Filed: Oct. 29, 2014

(86) PCT No.: PCT/IB2014/002280
§ 371 (c)(1),
(2) Date: Nov. 12, 2014

(87) PCT Pub. No.: WO2016/067069
PCT Pub. Date: May 6, 2016

(65) Prior Publication Data
US 2016/0122338 A1    May 5, 2016

(51) Int. Cl.
*G02B 5/23* (2006.01)
*C07D 471/04* (2006.01)
(Continued)

(52) U.S. Cl.
CPC ......... *C07D 471/04* (2013.01); *C07D 217/04* (2013.01); *C07D 401/04* (2013.01);
(Continued)

(58) Field of Classification Search
USPC ............ 252/586; 359/243; 544/238; 546/94, 546/144
See application file for complete search history.

(56) References Cited

U.S. PATENT DOCUMENTS 6,433,270 B1 * 8/2002 Rack ...................... B82Y 10/00
136/252

FOREIGN PATENT DOCUMENTS

DE    198 34 940    2/2000

OTHER PUBLICATIONS

Saleh A. Ahmed, Khalid S. Khairou, Basim H. Asghar, Hussni A. Muathen, Nariman M. A. Nahas, Hossa F. Alshareef, Photochromism of tetrahydroindolizines. Part XIV: synthesis of cis-fixed conjugated photochromic pyridazinopyrrolo [1,2-b]isoquinolines incorporating carbon-rich linkers, Tetrahedron Letters 55 (2014) 2190-2196, 2014. 2014 Elsevier Lt.*

(Continued)

*Primary Examiner* — Bijan Ahvazi
(74) *Attorney, Agent, or Firm* — Oblon, McClelland, Maier & Neustadt, L.L.P.

(57) ABSTRACT

Photochromic tetrahydroindolizines (THIs) bearing dihydroisoquinoline derivatives as heterocyclic bases and central fluorene groups have been synthesized via different chemical and photochemical pathways. Three alternative pathways for the synthesis of the target photochromic THI-based pyridazinopyrrolo[1,2-b]isoquinolines via in situ trapping with hydrazine hydrate are also provided. High product yields are obtained using different Sonogashira-mediated coupling reactions provided herein. Low temperature multichannel UV-vis and flash photolysis techniques were used to detect the photochromic and kinetic properties of the synthesized system.

18 Claims, 8 Drawing Sheets

(51) Int. Cl.

| | | |
|---|---|---|
| *C07D 217/04* | (2006.01) | |
| *C07D 401/04* | (2006.01) | |
| *G02F 1/01* | (2006.01) | |
| *C07D 471/10* | (2006.01) | |
| *C09B 57/00* | (2006.01) | |
| *G03C 1/685* | (2006.01) | |
| *G02F 1/03* | (2006.01) | |
| *G02F 1/07* | (2006.01) | |
| *C07D 401/00* | (2006.01) | |
| *C07D 403/00* | (2006.01) | |
| *C07D 405/00* | (2006.01) | |
| *C07D 409/00* | (2006.01) | |

(52) U.S. Cl.
CPC ............ *C07D 471/10* (2013.01); *C09B 57/00* (2013.01); *G02F 1/0126* (2013.01); *G03C 1/685* (2013.01)

(56) References Cited

OTHER PUBLICATIONS

International Search Report and Written Opinion issued Feb. 13, 2015 in PCT/IB2014/002280.

Saleh Abdel-Mgeed Ahmed, et al., "Photochromism of dihydroindolizines. Part 12: synthesis and photochromism of novel pi-conjugated rigid dihydroindolizines as potential molecular electronic devices" Tetrahedron, vol. 65, No. 7, XP025872493, Feb. 14, 2009, pp. 1373-1388.

Shrestha, T. B., "New insights in the photochromic spiro-dihydroindolizine/betaine-system", Photochem. Photobiol. Sci., vol. 7, pp. 1449-1456, 2008.

Ahmed, S. A., et al., "Photochromism of tetrahydroindolizines. Part XIV: synthesis of cis-fixed conjugated photochromic pyridazinopyrrolo [1,2-b] isoquinolines incorporating carbon-rich linkers", Tetrahedron Letters, vol. 55, pp. 2190-2196, 2014.

* cited by examiner

PHOTOCHROMIC TETRAHYDROINDOLIZINES

BACKGROUND OF THE INVENTION

Technical Field

The present invention relates to novel photochromic organic compounds, more specifically novel tetrahydroindolizines with photochromic properties, the synthesis of the photochromic organic compounds, and their use in devices such as optical memories and photoswitches.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Because of the potential applications of photochromic compounds in erasable optical memories and photoswitches, they have attracted significant attention (German Patent Application Publications DE 3823496 A1 19900118: Preparation of crown compounds for use in analytical chemistry, electronics, and fiber and film techniques; DE 3521432 A1 19861218: Indolizines as light-sensitive materials; DE 3320077 A1 19841206: Photochromic spiro compounds; DE 3220257 A1 19831201:Photochromic spiro[1,8-a-tetrahydroindolizines] and their use in radiation-sensitive materials; DE 2906193 A1 19800828: Photochromic spiro[1,8-a-dihydroindolizines] and their use in radiation-sensitive materials; Bouas-Laurent, H.; Dürr, H. Pure Appl. Chem. 2001, 73, 639-665; Dorion, G. H.; Wiebe, A. F. Photochromism; Focal Press: New York, 1970; Photochromism; Brown, G. H., Ed.; Wiley: New York, 1971; Dürr, H.; Bouas-Laurent, H. Photochromism: Molecules and Systems; Elsevier: Amsterdam, 1990; Crano, G. C.; Guglielmetti, R. Organic Photochromic and Thermochromic Compounds; Plenum Press: New York, 1999; McArdle, C. B. Applied Photochromic Polymer Systems; Blackie: Glasgow, 1992; Irie, M. Photo-Reactive Materials for Ultrahigh Density Optical Memory; Elsevier: Amsterdam, 1994; Guglielmeti, R.; Samat, A. Proceedings of the First International Symposium on Organic Photochromism, Molecular Crystals and Liquid Crystals, 1994, 246; Irie, M. In Molecular Switches; Feringa, B. L., Ed.; Wiley-VCH: Weinheim, 2001; pp 37-60; Iri, M. In Organic Photochromic and Thermochromic Compounds; Crano, J. C., Gugielmetti, R. J., Eds.; Plenum Press: New York, 1999; Vol. 1, pp 207-221. Gorodetsky, B.; Branda, N. Adv. Funct. Mater. 2007, 17, 786; Roberts, M. N.; Carling, C. J.; Nagle, J. K.; Branda, N.; Wolf, M. O. J. Am. Chem. Soc. 2009, 131, 16644. Li, Y. N.; Li, Q. Org. Lett. 2012, 14, 4362-4365; Lv, X. Y.; Wang, M. S.; Yang, C.; Wang, G. E.; Wang, S. H.; Lin, R. G.; Guo, G. C. Inorg. Chem. 2012, 51, 4015-4019; Kamiya, H.; Yanagisawa, S.; Hiroto, S.; Itami, K.; Shinokubo, H. Org. Lett. 2011, 13, 6394-6397; Chen, S. J.; Chen, L. J.; Yang, H. B.; Tian, H.; Zhu, W. H. J. Am. Chem. Soc. 2012, 134, 13596-13599; Sciascia, C.; Castagna, R.; Dekermenjian, M.; Martel, R.; Kandada, A. S.; Fonzo, F. D.; Bianco, A.; Bertarelli, C.; Meneghetti, M.; Lanzani, G. J. Phys. Chem. C 2012, 116, 19483-19489; Ishibashi, Y.; Umesato, T.; Kobatake, S.; Irie, M.; Miyasaka, H. J. Phys. Chem. C 2012, 116, 4862-4869; Bertarelli, C.; Bianco, A.; D'Amore, F.; Gallazzi, M. C.; Zerbi, G.; Adv. Funct. Alater. 2004, 14, 357-363; Fukaminato, T.; Doi, T.; Tamaoki, N.; Okuno, K.; Ishibashi, Y.; Miyasaka, H.; Irie, M. J. Am. Chem. Soc. 2011, 133, 4984-4990; Heremans, P.; Gelinck, G. H.; Miiller, R.; Baeg, K.; Kim, D.; Noh, Y. Chem. Mater. 2011, 23, 341-358; Herder, M.; Patzel, M.; Grubert, L.; Hecht, S. Chem. Commun. 2011, 460-462; Kim, M. S.; Maruyama, H.; Kawat, T.; Irie., M. Chem. Mater. 2003, 15, 4539-4543; Sanz-Menez, N.; Monnier, V.; Colombier, I.; Baldeck, B. L.; Irie, M.; Ibanez, A. Dyes Pigments 2011, 89, 241-245; Liu, G.; Pu, S. Z.; Wang, X. M.; Liu, W. J.; Fan, C. B. Dyes Pigments 2011, 90, 89-99; Tsivgoulis, G.; Lehn, J.-M. Angew. Chem., Int. Ed. Engl. 1995, 34, 1119-1122; Tsujioka, T.; Hamada, Y.; Shibata, K. Appl. Phys. Lett. 2001, 78, 2282-2284; Wojtyk, J. T.; Buncel, E.; Kazmaier, P. M. Chem. Commun. 1998, 1703-1704; Tanaka, M.; Nakamura, M.; Salhin, M. A. A.; Ikeda, T.; Kamada, K.; Ando, H. J. Org. Chem. 2001, 66, 1533-1537—each incorporated herein by reference in its entirety). Upon light irradiation, photochromic molecules exhibit reversible color and structural changes. These molecules have the ability to interconvert between different isomers having unique absorption spectra when stimulated with light. In these systems, the changes in the electronic patterns are responsible for the changes in color and in variations in other physical properties such as luminescence, electronic conductance, refractive index, optical rotation, and viscosity. The photomodulation of these properties has the potential to significantly advance optoelectronic technologies such as waveguides, read/write/erase optical information storage systems and actuators. Photochromic molecules can be employed to modulate various physicochemical properties upon light irradiation, and they have received remarkable attention for their potential applications as photoswitches and optical memory systems (Biteau, J.; Chaput, F.; Lahlil, K.; Boilot, J.-P.; Tsivgoulis, G. M.; Lehn, J.-M.; Darracq, B.; Marois, C.; Lévy, Y. Chem. Mater. 1998, 10, 1945-1950; van Delden, R. A.; ter Wiel, K. K. J.; Feringa, B.-L. Chem. Commun. 2004, 200-201; Feringa, B.-L.; van Delden, R. A.; ter Wiel, M. K. J. Molecular Switches; Wiley-VCH: Weinheim, 2001; pp 123-164; Murguly, E.; Norsten, T.; Branda, N. R. Angew. Chem., Int. Ed. 2001, 40, 1752-1755; Norsten, T. B.; Branda, N. R.; Adv. Mater. 2001, 13, 347-349; Kawai, S.; Yamaguchi, T.; Kato, T.; Hatano, S.; Abe, J. Dyes Pigments 2012, 92, 872-876; Kawai, T.; Kunitake, K.; Irie, M. Chem. Lett. 1999, 905-906; Kim, E.; Choi, Y.-K.; Lee, M.-H. Macromolecules 1999, 32, 4855-4860; Moniruzzaman, M.; Sabey, C. J.; Fernando, G. F. Macromolecules 2004, 37, 2572-2577; Lucas, L. N.; van Esch, J.; Kellogg, R. M.; Feringa, B.-L. Chem. Commun. 2001, 759-760; Kang, J. W.; Kim, J.-J.; Kim, E. Appl. Phys. Lett. 2002, 80, 1710-1713; Wang, C.; Batsanov, A. S.; Bryce, M. R.; Sage, I. Synthesis 2003, 2089-2095; Wang, C.; Pålsson, L.-O.; Batsanov, A. S.; Bryce, M. R. J. Am. Chem. Soc. 2006, 128, 3789-799; Kang, J. W.; Kim, J.-J.; Kim, E. Opt. Mater. 2002, 21, 543-548; Myles, A. J.; Branda, N. R. Adv. Funct. Mater. 2002, 12, 167-173; Hugel, T.; Holland, N. B.; Cattani, A.; Moroder, L.; Seitz, M.; Gaub, H. E. Science 2002, 296, 1103-1106; Alonso, M.; Reboto, V.; Guiscardo, L.; San Martin, A.; Rodriguez-Cabello, J. C. Macromolecules 2000, 33, 9480-9482; Wigglesworth, T. G.; Myles, A. J.; Branda, N. R. Eur. J. Org. Chem. 2005, 1233-1238; Horii, T.; Abe, Y.; Nakao, R. J. Photochem. Photobiol., A 2011, 144, 119-129; Peters, A.; Vitols, C.; McDonald, R.; Branda, N. R. Org. Lett. 2002, 5, 1183-1186; Kalyanasundaram, K.; Grätzel, M. Coord. Chem. Rev. 1998, 347; Argazzi, R.; Bignozzi, C. A.; Heimer, T. A.; Castellano, F. N.; Meyer, G. J. Inorg. Chem. 1994, 33, 5741; Tomasulo, M.; Yildiz, I.; Raymo, F. M. Inorg. Chim. Acta 2007, 360, 938-944; Deniz, E.; Cusido, J.; Swaminathan, S.; Battal, M.; Impellizzeri, S.; Sortino, S.; Raymo, F. M. J. Photochem. Photobiol., A 2012, 229, 20-28 Ahmed, S.

A.; Weber, C.; Hozien, Z. A.; Hassan, Kh. M.; Abdel-Wahab, A. A.; Dürr, H. *Unpublished results*; Ahmed, S. A.; *Ph. D Thesis*, Saarland-Assiut universities, 2000; Burtscher, P.; Dürr, H.; Rheinberger, V.; Salz, U.; German PatDE, 1995, 195200160; Dürr, H.; Gross, H.; Zils, K D. *Deutsche Offenlegungs Schrift Pat.*, 1983, 3220275A1; Burtscher, B.; Dürr, H.; Rheinberger, V.; Salz. U.; *IVOCLAR German Pat.*, 1995, 195200160—each incorporated by reference herein in its entirety). Since the pioneering discovery of photochromic dihydroindolizines (DHIs) and tetrahydroindolizines (THIs), they have been considered as very interesting photochromic families because of their specific properties such as high photo-fatigue resistance, broad absorption spectra in the visible region, high sensitivity to activation with light, and high photochromic reactivity (Dürr, H. Angew. Chem., Int. Ed. 1989, 28, 413-438; Dürr, H. Wiss. Zeitschr. TH Leuna-Merseburg 1984, 26, 664-671; Dürr, H.; Gross, H.; Zils, K. D. DE 3220257, 1983; Chem. Abstr. 1984, 100, 120909; Dürr, H.; Jönsson, H. P.; Bleisinger, H.; Scheidhauer, P.; Dürr, H.; Wintgens, V.; Valat, P.; Kossanyi, J. *J. Org. Chem.* 1998, 63, 990-1000; Scheidhauer, P.; Münzmay, T.; Spang, P. DE 3521432, 1986; Chem. Abstr. 1987, 106, 102089; Dürr, H.; Janzen, K. P.; Thome, A.; Braun, B. DE 3823496 A1, 1990; Chem. Abstr. 1990, 113, 132224; Dürr, H.; Gross, H.; Zils, K. D.; Hauck, G.; Hermann, H. Chem. Ber. 1983, 116, 3915-3925; Dürr, H.; Spang. P. DE 3320077, 1984; Dürr, H.; Spang, P.; *Deutsche Offenlegungs Schrift Pat.* 1984, 32 20 2571; Dürr. H.; Jönsson, H.; Scheidhauer, P.; Münzmay, T, Spang, P. *Deutsche Offenlegungs Schrift Pat.* 1985, 35214325 Chem. Abstr. 1985, 102, 205414; Fromm, R.; Ahmed, S. A.; Hartmann, Th.; Huch, V.; Abdel-Wahab, A. A.; Dürr, H. Eur. J. Org. Chem. 2001, 21, 4077-4080; Weber, C.; Rustemeyer, F.; Dürr, H. Adv. Mater. 1998, 10, 1348-1351; Andreis, C.; Dürr, H.; Wintgens, V.; Valat, P.; Kossanyi, J. Chem. Eur. J. 1997, 3, 509-516; Ahmed, S. A.; Abdel-Wahab, A. A.; Dürr, H. In CRC Handbook of Organic Photochemistry and Photobiology, Chapter 96; Horspool, W. M., Lenci, F., Eds., 2nd ed.; CRC Press: New York, 2003; pp 1-25—each incorporated by reference herein in its entirety).

The exploration of new di- and tetrahydroindolizine structures with improved properties has received significant attention in organic materials science (Dürr, H.; Janzen, K. P.; Thome, A.; Braun, B. DE 3823496 A1, 1990; Chem. Abstr. 1990, 113, 132224; Dürr, H.; Gross, H.; Zils, K. D.; Hauck, G.; Hermann, H. Chem. Ber. 1983, 116, 3915-3925; Dürr, H.; Spang. P. DE 3320077, 1984; Chem. Abstr. 1985, 102, 205414; Fromm, R.; Ahmed, S. A.; Hartmann, Th.; Huch, V.; Abdel-Wahab, A. A.; Dürr, H. Eur. J. Org. Chem. 2001, 21, 4077-4080; Weber, C.; Rustemeyer, F.; Dürr, H. Adv. Mater. 1998, 10, 1348-1351; Andreis, C.; Dürr, H.; Wintgens, V.; Valat, P.; Kossanyi, J. Chem. Eur. J. 1997, 3, 509-516; Ahmed, S. A.; Abdel-Wahab, A. A.; Dürr, H. In CRC Handbook of Organic Photochemistry and Photobiology, Chapter 96; Horspool, W. M., Lenci, F., Eds., 2nd ed.; CRC Press: New York, 2003; pp 1-25; Ahmed, S. A.; Hartmann, Th.; Huch, V.; Dürr, H.; Abdel-Wahab, A. A. J. Phys. Org. Chem. 2000, 13, 539-548; Tan, Y.; Ahmed, S. A.; Dürr, H.; Huch, V.; Abdel-Wahab, A. A. Chem. Commun. 2001, 1246-1247—each incorporated by reference herein in its entirety). Suitable functionalization in both regions (region A is fluorene, region B is the ester or cyano groups, and region C is the heterocyclic base part) of the DHI skeleton with different substituents can modify effectively the photochromic behavior of dihydroindolizines (Ahmed, S. A. Mol. Cryst. Liq. Cryst. 2005, 430, 295-300; Ahmed, S. A.; Dürr, H. Mol. Cryst. Liq. Cryst. 2005, 431, 275-280; Ahmed, S. A. Monatsh. Chem. 2004, 135, 1173-1188; Ahmed, S. A.; Abdel-Wahab, A. A.; Dürr, H. J. Photochem. Photobiol. 2003, 154, 131-144; Ahmed, S. A. J. Phys. Org. Chem. 2002, 15, 392-402; Ahmed, S. A. J. Phys. Org. Chem. 2006, 19, 402-414; Ahmed, S. A. J. Phys. Org. Chem. 2007, 20, 564-588; Ahmed, S. A.; Hartmann, Th.; Dürr, H. J. Photochem. Photobiol. 2008, 200, 50-56; Ahmed, S. A.; Pozzo, J. L. J. Photochem. Photobiol. 2008, 200, 57-67—each incorporated by reference herein in its entirety).

The position of the substituents is also important for fine-tuning of their optoelectronic properties (Andreis, C.; Dürr, H.; Wintgens, V.; Valat, P.; Kossanyi, J. Chem. Eur. J. 1997, 3, 509-516; Ahmed, S. A.; Abdel-Wahab, A. A.; Dürr, H. In CRC Handbook of Organic Photochemistry and Photobiology, Chapter 96; Horspool, W. M., Lenci, F., Eds., 2nd ed.; CRC Press: New York, 2003; pp 1-25; Ahmed, S. A.; Hartmann, Th.; Huch, V.; Dürr, H.; Abdel-Wahab, A. A. J. Phys. Org. Chem. 2000, 13, 539-548; Tan, Y.; Ahmed, S. A.; Dürr, H.; Huch, V.; Abdel-Wahab, A. A. Chem. Commun. 2001, 1246-1247; Ahmed, S. A. Mol. Cryst. Liq. Cryst. 2005, 430, 295-300; Ahmed, S. A.; Dürr, H. Mol. Cryst. Liq. Cryst. 2005, 431, 275-280; Ahmed, S. A. Monatsh. Chem. 2004, 135, 1173-1188; Ahmed, S. A.; Abdel-Wahab, A. A.; Dürr, H. J. Photochem. Photobiol. 2003, 154, 131-144; Ahmed, S. A. J. Phys. Org. Chem. 2002, 15, 392-402; Ahmed, S. A. J. Phys. Org. Chem. 2006, 19, 402-414; Ahmed, S. A. J. Phys. Org. Chem. 2007, 20, 564-588; Ahmed, S. A.; Hartmann, Th.; Dürr, H. J. Photochem. Photobiol. 2008, 200, 50-56; Ahmed, S. A.; Pozzo, J. L. J. Photochem. Photobiol. 2008, 200, 57-67—each incorporated by reference herein in its entirety). So far, related research has been mainly focused on the effects of substitutents on the fluorene and pyridazine moieties in the dihydroindolizine photochromes (Dürr, H.; Janzen, K. P.; Thome, A.; Braun, B. DE 3823496 A1, 1990; Chem. Abstr. 1990, 113, 132224; Dürr, H.; Gross, H.; Zils, K. D.; Hauck, G.; Hermann, H. Chem. Ber. 1983, 116, 3915-3925; Dürr, H.; Spang. P. DE 3320077, 1984; Chem. Abstr. 1985, 102, 205414; Fromm, R.; Ahmed, S. A.; Hartmann, Th.; Huch, V.; Abdel-Wahab, A. A.; Dürr, H. Eur. J. Org. Chem. 2001, 21, 4077-4080; Weber, C.; Rustemeyer, F.; Dürr, H. Adv. Mater. 1998, 10, 1348-1351; Andreis, C.; Dürr, H.; Wintgens, V.; Valat, P.; Kossanyi, J. Chem. Eur. J. 1997, 3, 509-516; Ahmed, S. A.; Abdel-Wahab, A. A.; Dürr, H. In CRC Handbook of Organic Photochemistry and Photobiology, Chapter 96; Horspool, W. M., Lenci, F., Eds., 2nd ed.; CRC Press: New York, 2003; pp 1-25; Ahmed, S. A.; Hartmann, Th.; Huch, V.; Dürr, H.; Abdel-Wahab, A. A. J. Phys. Org. Chem. 2000, 13, 539-548; Tan, Y.; Ahmed, S. A.; Dürr, H.; Huch, V.; Abdel-Wahab, A. A. Chem. Commun. 2001, 1246-1247; Ahmed, S. A. Mol. Cryst. Liq. Cryst. 2005, 430, 295-300; Ahmed, S. A.; Dürr, H. Mol. Cryst. Liq. Cryst. 2005, 431, 275-280; Ahmed, S. A. Monatsh. Chem. 2004, 135, 1173-1188; Ahmed, S. A.; Abdel-Wahab, A. A.; Dürr, H. J. Photochem. Photobiol. 2003, 154, 131-144; Ahmed, S. A. J. Phys. Org. Chem. 2002, 15, 392-402; Ahmed, S. A. J. Phys. Org. Chem. 2006, 19, 402-414; Ahmed, S. A. J. Phys. Org. Chem. 2007, 20, 564-588; Ahmed, S. A.; Hartmann, Th.; Dürr, H. J. Photochem. Photobiol. 2008, 200, 50-56; Ahmed, S. A.; Pozzo, J. L. J. Photochem. Photobiol. 2008, 200, 57-67; Dürr, H. Chimica 1994, 514-515; Masson, J.-F.; Hartmann, Th.; Dürr, H.; Booksh, K. S. Opt. Mater. 2004, 27, 435-439; Terazono, Y.; Kodis, J.; Andreasson, J.; Jeong, G.; Brune, A.; Hartmann, Th.; Dürr, H.; Moore, A. L.; Moore, Th. M.; Gust, D. J. Phys. Chem. 2004, 108, 1812-1814; Kodis, G.; Liddell, P. A.; de la Garza, L.; Clausen, P. C.; Lindsey, J. S.; Moore, A. L.; Moore, T. A.; Gust, D. J.

Phys. Chem. A 2002, 106, 2036-2048; Shrestha, T. B.; Melin, J.; Liu, Y.; Dolgounitcheva, O.; Zakrzewski, V. G.; Pokhrel, M. R.; Gogritchiani, E.; Ortiz, J. V.; Turro, C.; Bossmann, S. H. Photochem. Photobiol. Sci. 2008, 7, 1449-1456; Shrestha, T. B.; Kalita, M.; Pokhrel, M. J.; Liu, Y.; Troyer, D. L.; Turro, C.; Bossmann, S. H.; Dürr, H. J. Org. Chem. 2013, 78, 1903-1909; Gogritchiani, E.; Hartmann, Th.; Palm, B.; Samsoniya, Sh.; Dürr, H. J. Photochem. Photobiol., B 2002, 67, 18-22; Ahmed, S. A. Tetrahedron 2009, 65, 1373-1388; Ahmed, S. A.; Khairou, K. S.; Abdel-Wahab, A. A.; Hozien, Z. A.; Dürr, H. Tetrahedron Lett. 2012, 53, 4397-4401; Ahmed, S. A.; Al-Raqa, S. Y.; Moussa, Z.; Hozien, Z. A.; Abdel-Wahab, A. A.; Al-Simaree, A. A.; Al-Amri, S. N.; Soliman, A. S.; Dürr, H. Tetrahedron 2011, 67, 7173-7184—each incorporated by reference herein in its entirety).

Reports on photochromic tetrahydroindolizines (THIs) are few. Such molecules undergo a photoinduced change of color in solution, solid state, and in polymer matrices when exposed to UV irradiation or direct sunlight, and return to their initial state when the illumination ceases, normally via a thermal pathway. The photochromic behavior of THIs (FIG. 1) is based on a reversible pyrroline ring-opening, induced by light, which converts a colorless form (usually named the 'closed form') into the colored form (betaine form) (Ahmed, S. A. Mol. Cryst. Liq. Cryst. 2005, 430, 295-300; Ahmed, S. A.; Dürr, H. Mol. Cryst. Liq. Cryst. 2005, 431, 275-280; Ahmed, S. A. Monatsh. Chem. 2004, 135, 1173-1188; Ahmed, S. A.; Abdel-Wahab, A. A.; Dürr, H. J. Photochem. Photobiol. 2003, 154, 131-144; Ahmed, S. A. J. Phys. Org. Chem. 2002, 15, 392-402; Ahmed, S. A. Phys. Org. Chem. 2006, 19, 402-414—each incorporated by reference herein in its entirety).

Few reports on photochromic THIs showed that the thermal reverse reaction, the 1,5-electrocyclization from the ring-open betaine to the THI shows rates extending from milliseconds to several weeks (Ahmed, S. A. Mol. Cryst. Liq. Cryst. 2005, 430, 295-300; Ahmed, S. A.; Dürr, H. Mol. Cryst. Liq. Cryst. 2005, 431, 275-280; Ahmed, S. A. Monatsh. Chem. 2004, 135, 1173-1188; Ahmed, S. A.; Abdel-Wahab, A. A.; Dürr, H. J. Photochem. Photobiol. 2003, 154, 131-144; Ahmed, S. A. J. Phys. Org. Chem. 2002, 15, 392-402—each incorporated by reference herein in its entirety), depending on the substituents and structure of the molecule involved. This interesting wide range in the life-time of the colored form allows these molecules to find many versatile applications as shown by DHI photochromes (Ahmed, S. A. Tetrahedron 2009, 65, 1373-1388; Ahmed, S. A.; Khairou, K. S.; Abdel-Wahab, A. A.; Hozien, Z. A.; Dürr, H. Tetrahedron Lett. 2012, 53, 4397-4401; Ahmed, S. A.; Al-Raqa, S. Y.; Moussa, Z.; Hozien, Z. A.; Abdel-Wahab, A. A.; Al-Simaree, A. A.; Al-Amri, S. N.; Soliman, A. S.; Dürr, H. Tetrahedron 2011, 67, 7173-7184; DE 3823496 A1 19900118: Preparation of crown compounds for use in analytical chemistry, electronics, and fiber and film techniques; DE 3521432 A1 19861218: Indolizines as light-sensitive materials DE 3320077 A1 19841206: Photochromic spiro compounds; DE 3220257 A1 19831201: Photochromic spiro[1,8-a-tetrahydroindolizines] and their use in radiation-sensitive materials; DE 2906193 A1 19800828: Photochromic spiro[1,8-a-dihydroindolizines] and their use in radiation-sensitive materials—each incorporated by reference herein in its entirety).

BRIEF SUMMARY OF THE INVENTION

Described are photochromic compounds having the following Formulas I-IV:

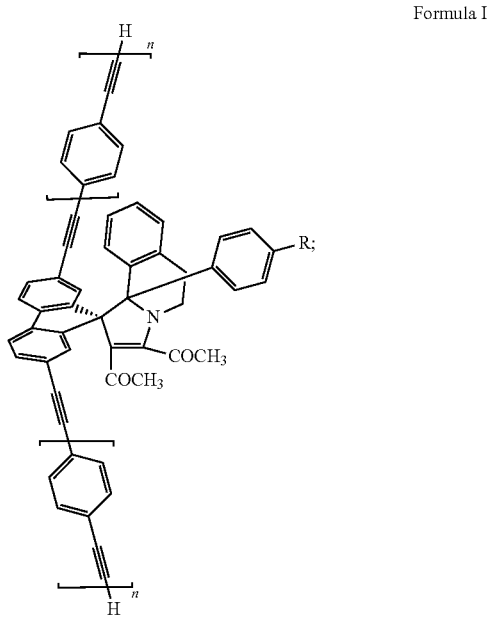

Formula I

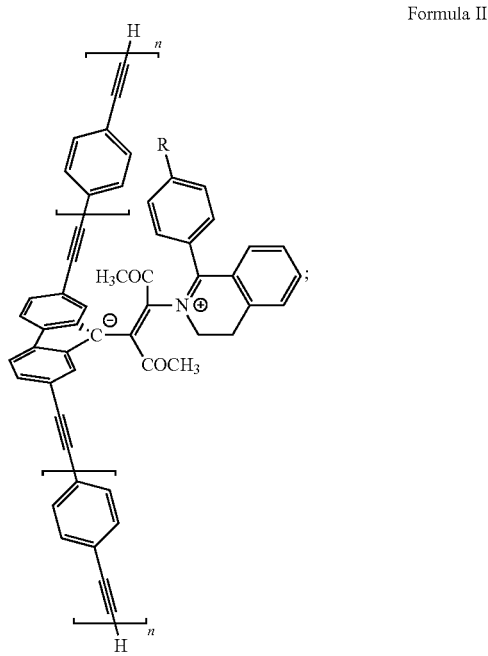

Formula II

-continued

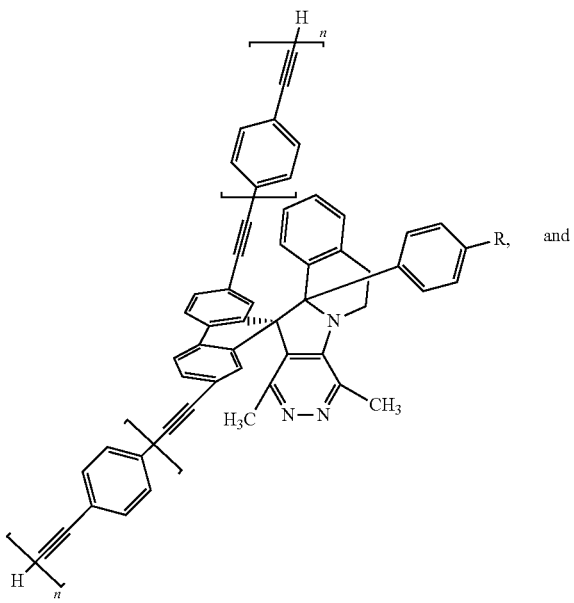

Formula III

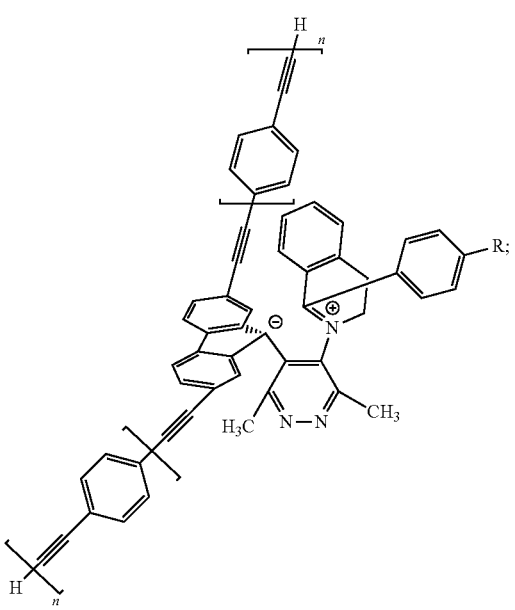

Formula IV wherein: n is an integer selected from 0, 1 or 2 and R is selected from hydrogen, alkyl, alkenyl, aryl, arylakyl, acyloxy, heteroaryl, amino, acylamino, alkylamino, acyl, hydroxy, alkoxy, halo and cyano.

Examples of these compounds, photochromic compositions comprising at least one compound of Formulas I-IV and different methods of synthesizing these compounds are also provided.

Photochromic devices including optical memories and photoswitches using the photochromic compositions are also described.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
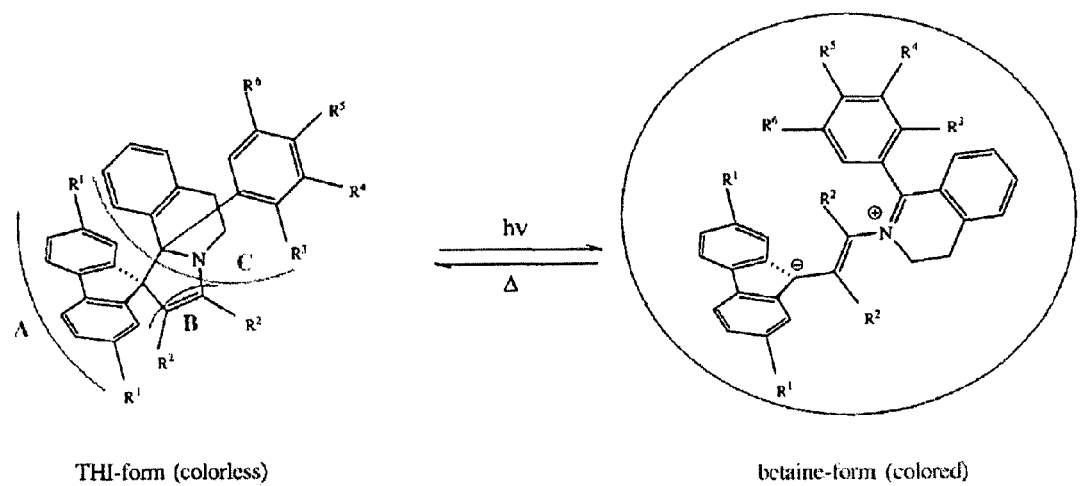
FIG. 1 is a schematic diagram illustrating the phenomenon of ring-opening upon UV irradiation and ring-closure in THI photochromes.

Referring now to the drawings, wherein like reference numerals designate identical or corresponding parts throughout the several views.

The present invention relates to the synthesis of novel, highly conjugated, photochromic tetrahydroindolizines (THIs) via palladium-mediated Sonogashira coupling reactions. THIs exhibit kinetics of 1,5-electrocyclization that provide different fading rates which suit important commercial and industrial applications.

The disclosed photochromic compounds have the following Formulas I-IV:

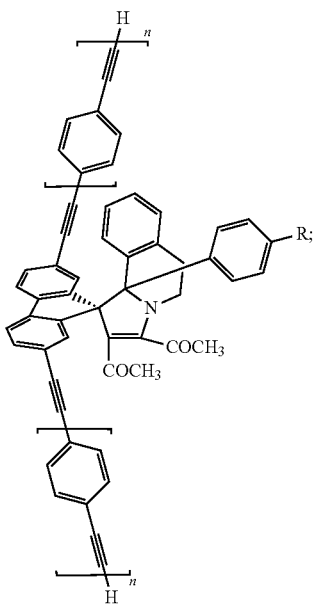

Formula I

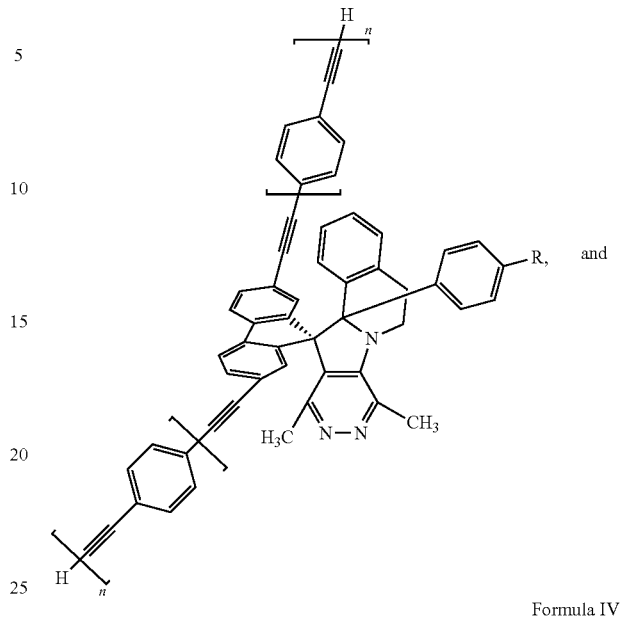

Formula III

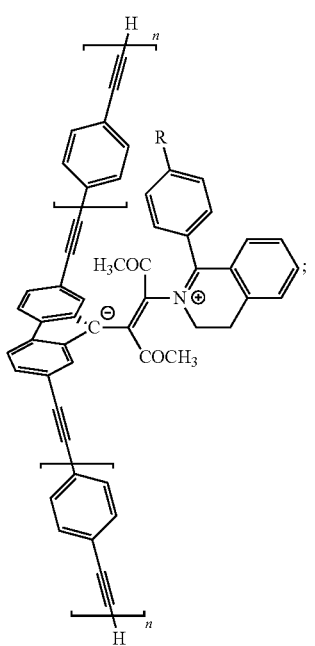

Formula II

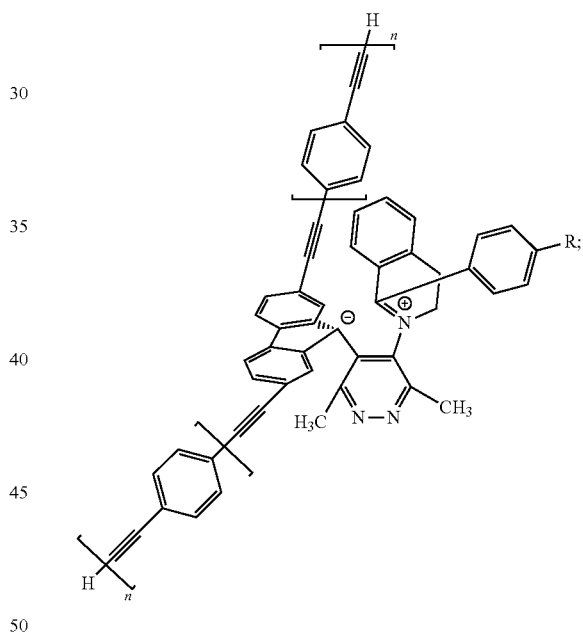

Formula IV wherein: n is an integer selected from 0, 1 or 2 and R is selected from hydrogen, alkyl, alkenyl, aryl, arylakyl, acyloxy, heteroaryl, amino, acylamino, alkylamino, acyl, hydroxy, alkoxy, halo and cyano.

Photochromic compositions comprising at least one compound of Formulas I-IV and different methods of synthesizing these compounds/composition are also disclosed. Photochromic devices including optical memories and photoswitches using the photochromic compositions are also described.

In a preferred embodiment, a photochromic THI compound disclosed in the present invention has a central fluorene group substituted with dihydroisoquinoline derivatives as heterocyclic bases.

Examples of the novel photochromic THIs contemplated within the scope of the present invention include:

1-((2'S, 10b'R)-2'-methyl-10b'-phenethyl-3',5',6',10b'-tetrahydro-2'H-spiro[fluorene-9, 1'-pyrrolo[2,1-a]isoquinolin]-3'-yl)ethanone;

1-((2'S,10b'R)-2'-methyl-10b'-(4-methylphenethyl)-3',5',6',10b'-tetrahydro-2'H-spiro[fluorene-9,1'-pyrrolo[2,1-a]isoquinolin]-3'-yl)ethanone;

1-((2'S,10b'R)-10b'-(4-fluorophenethyl)-2'-methyl-3',5',6',10b'-tetrahydro-2'H-spiro[fluorene-9,1'-pyrrolo[2,1-a]isoquinolin]-3'-yl)ethanone;

4-(2-((2'S, 10b'R)-3'-acetyl-2'-methyl-3',5',6',10b'-tetrahydro-2'H-spiro[fluorene-9,1'-pyrrolo[2,1-a]isoquinoline]-10b'-yl)ethyl)benzonitrile;

1-((2'S,10b'R)-2'-methyl-10b'-phenethyl-2,7-diphenyl-3',5',6',10b'-tetrahydro-2'H-spiro[fluorene-9, 1'-pyrrolo[2,1-a]isoquinolin]-3'-yl)ethanone;

1-((2'S,10b'R)-2'-methyl-10b'-(4-methylphenethyl)-2,7-diphenyl-3',5',6',10b'-tetrahydro-2'H-spiro[fluorene-9,1'-pyrrolo[2,1-a]isoquinolin]-3'-yl)ethanone;

1-((2'S,10b'R)-10b'-(4-fluorophenethyl)-2'-methyl-2,7-diphenyl-3',5',6',10b'-tetrahydro-2'H-spiro[fluorene-9,1'-pyrrolo[2,1-a]isoquinolin]-3'-yl)ethanone;

4-(2-((2'S, 10b'R)-3'-acetyl-2'-methyl-2,7-diphenyl-3',5',6',10b'-tetrahydro-2'H-spiro[fluorene-9,1'-pyrrolo[2,1-a]isoquinoline]-10b'-yl)ethyl)benzonitrile;

1-((2'S,10b'R)-2'-methyl-10b'-phenethyl-2,3,6,7-tetraphenyl-3',5',6',10b'-tetrahydro-2'H-spiro[fluorene-9,1'-pyrrolo[2,1-a]isoquinolin]-3'-yl)ethanone;

1-((2'S,10b'R)-2'-methyl-10b'-(4-methylphenethyl)-2,3,6,7-tetraphenyl-3',5',6',10b'-tetrahydro-2'H-spiro[fluorene-9, 1'-pyrrolo[2,1-a]isoquinolin]-3'-yl)ethanone;

1-((2'S,10b'R)-2'-methyl-10b'-(4-methylphenethyl)-2,3,6,7-tetraphenyl-3',5',6',10b'-tetrahydro-2'H-spiro[fluorene-9, 1'-pyrrolo[2,1-a]isoquinolin]-3'-yl)ethanone;

1-((2'S,10b'R)-2'-methyl-10b'-(4-methylphenethyl)-2,3,6,7-tetraphenyl-3',5',6',10b'-tetrahydro-2'H-spiro[fluorene-9, 1'-pyrrolo[2,1-a]isoquinolin]-3'-yl)ethanone;

(Z)-9-(2,5-dioxo-4-(1-phenyl-3,4-dihydroisoquinolin-2-ium-2-yl)hex-3-en-3-yl)-9H-fluoren-9-ide;

(Z)-9-(2,5-dioxo-4-(1-(p-tolyl)-3,4-dihydroisoquinolin-2-ium-2-yl)hex-3-en-3-yl)-9H-fluoren-9-ide;

(Z)-9-(4-(1-(4-fluorophenyl)-3,4-dihydroisoquinolin-2-ium-2-yl)-2,5-dioxohex-3-en-3-yl)-9H-fluoren-9-ide;

(Z)-9-(4-(1-(4-cyanophenyl)-3,4-dihydroisoquinolin-2-ium-2-yl)-2, 5-dioxohex-3-en-3-yl)-9H-fluoren-9-ide;

(Z)-9-(2,5-dioxo-4-(1-phenyl-3,4-dihydroisoquinolin-2-ium-2-yl)hex-3-en-3-yl)-2,7-diphenyl-9H-fluoren-9-ide;

(Z)-9-(2,5-dioxo-4-(1-(p-tolyl)-3,4-dihydroisoquinolin-2-ium-2-yl)hex-3-en-3-yl)-2,7-diphenyl-9H-fluoren-9-ide;

(Z)-9-(4-(1-(4-fluorophenyl)-3,4-dihydroisoquinolin-2-ium-2-yl)-2, 5-dioxohex-3-en-3-yl)-2,7-diphenyl-9H-fluoren-9-ide;

(Z)-9-(4-(1-(4-cyanophenyl)-3,4-dihydroisoquinolin-2-ium-2-yl)-2,5-dioxohex-3-en-3-yl)-2,7-diphenyl-9H-fluoren-9-ide;

(Z)-9-(2,5-dioxo-4-(1-phenyl-3,4-dihydroisoquinolin-2-ium-2-yl)hex-3-en-3-yl)-2,3,6,7-tetraphenyl-9H-fluoren-9-ide;

(Z)-9-(2,5-dioxo-4-(1-(p-tolyl)-3,4-dihydroisoquinolin-2-ium-2-yl)hex-3-en-3-yl)-2,3,6,7-tetraphenyl-9H-fluoren-9-ide;

(Z)-9-(4-(1-(4-fluorophenyl)-3,4-dihydroisoquinolin-2-ium-2-yl)-2, 5-dioxohex-3-en-3-yl)-2,3,6,7-tetraphenyl-9H-fluoren-9-ide;

(Z)-9-(4-(1-(4-cyanophenyl)-3,4-dihydroisoquinolin-2-ium-2-yl)-2, 5-dioxohex-3-en-3-yl)-2,3,6,7-tetraphenyl-9H-fluoren-9-ide;

8',11'-dimethyl-12a'-phenethyl-6',12a'-dihydro-5'H-spiro[fluorene-9,12'-pyridazino[4',5':4,5]pyrrolo[2,1-a]isoquinoline];

8',11'-dimethyl-12a'-(4-methylphenethyl)-6',12a'-dihydro-5'H-spiro[fluorene-9,12'-pyridazino[4',5':4,5]pyrrolo[2,1-a]isoquinoline];

12a'-(4-fluorophenethyl)-8',11'-dimethyl-6',12a'-dihydro-5'H-spiro[fluorene-9,12'-pyridazino[4',5':4,5]pyrrolo[2,1-a]isoquinoline];

4-(2-(8',11'-dimethyl-6',12a'-dihydro-5'H-spiro[fluorene-9,12'-pyridazino[4',5':4,5]pyrrolo[2,1-a]isoquinolin]-12a'-yl)ethyl)benzonitrile;

8',11'-dimethyl-12a'-phenethyl-2,7-diphenyl-6',12a'-dihydro-5'H-spiro[fluorene-9,12'-pyridazino[4',5':4,5]pyrrolo[2,1-a]isoquinoline];

8',11'-dimethyl-12a'-(4-methylphenethyl)-2,7-diphenyl-6',12a'-dihydro-5'H-spiro[fluorene-9,12'-pyridazino[4',5':4,5]pyrrolo[2,1-a]isoquinoline]

12a'-(4-fluorophenethyl)-8',11'-dimethyl-2,7-diphenyl-6',12a'-dihydro-5'H-spiro[fluorene-9,12'-pyridazino[4',5':4,5]pyrrolo[2,1-a]isoquinoline];

4-(2-(8',11'-dimethyl-2,7-diphenyl-6',12a'-dihydro-5'H-spiro[fluorene-9,12'-pyridazino[4',5':4,5]pyrrolo[2,1-a]isoquinolin]-12a'-yl)ethyl)benzonitrile'

8',11'-dimethyl-12a'-phenethyl-2,3,6,7-tetraphenyl-6',12a'-dihydro-5'H-spiro[fluorene-9,12'-pyridazino[4',5':4,5]pyrrolo[2,1-a]isoquinoline];

8',11'-dimethyl-12a'-(4-methylphenethyl)-2,3,6,7-tetraphenyl-6',12a'-dihydro-5'H-spiro[fluorene-9,12'-pyridazino[4',5':4,5]pyrrolo[2,1-a]isoquinoline];

12a'-(4-fluorophenethyl)-8',11'-dimethyl-2,3,6,7-tetraphenyl-6',12a'-dihydro-5'H-spiro[fluorene-9,12'-pyridazino[4',5':4,5]pyrrolo[2,1-a]isoquinoline];

4-(2-(8',11'-dimethyl-2,3,6,7-tetraphenyl-6',12a'-dihydro-5'H-spiro[fluorene-9,12'-pyridazino[4',5':4,5]pyrrolo[2,1-a]isoquinolin]-12a'-yl)ethyl)benzonitrile;

9-(3,6-dimethyl-5-(1-phenethyl-3,4-dihydroisoquinolin-2-ium-2-yl)pyridazin-4-yl)-9H-fluoren-9-ide;

9-(3,6-dimethyl-5-(1-(4-methylphenethyl)-3,4-dihydroisoquinolin-2-ium-2-yl)pyridazin-4-yl)-9H-fluoren-9-ide;

9-(5-(1-(4-fluorophenethyl)-3,4-dihydroisoquinolin-2-ium-2-yl)-3,6-dimethylpyridazin-4-yl)-9H-fluoren-9-ide;

9-(5-(1-(4-cyanophenethyl)-3,4-dihydroisoquinolin-2-ium-2-yl)-3,6-dimethylpyridazin-4-yl)-9H-fluoren-9-ide;

9-(3,6-dimethyl-5-(1-phenethyl-3,4-dihydroisoquinolin-2-ium-2-yl)pyridazin-4-yl)-2,7-diphenyl-9H-fluoren-9-ide;

9-(3,6-dimethyl-5-(1-(4-methylphenethyl)-3,4-dihydroisoquinolin-2-ium-2-yl)pyridazin-4-yl)-2,7-diphenyl-9H-fluoren-9-ide;

9-(5-(1-(4-fluorophenethyl)-3,4-dihydroisoquinolin-2-ium-2-yl)-3,6-dimethylpyridazin-4-yl)-2,7-diphenyl-9H-fluoren-9-ide;

9-(5-(1-(4-cyanophenethyl)-3,4-dihydroisoquinolin-2-ium-2-yl)-3,6-dimethylpyridazin-4-yl)-2,7-diphenyl-9H-fluoren-9-ide;

9-(3,6-dimethyl-5-(1-phenethyl-3,4-dihydroisoquinolin-2-ium-2-yl)pyridazin-4-yl)-2,3,6,7-tetraphenyl-9H-fluoren-9-ide;

9-(3, 6-dimethyl-5-(1-(4-methylphenethyl)-3,4-dihydroisoquinolin-2-ium-2-yl)pyridazin-4-yl)-2,3,6,7-tetraphenyl-9H-fluoren-9-ide;

9-(5-(1-(4-fluorophenethyl)-3,4-dihydroisoquinolin-2-ium-2-yl)-3,6-dimethylpyridazin-4-yl)-2,3,6,7-tetraphenyl-9H-fluoren-9-ide; and 9-(5-(1-(4-cyanophenethyl)-3,4-dihydroisoquinolin-2-ium-2-yl)-3,6-dimethylpyridazin-4-yl)-2,3,6,7-tetraphenyl-9H-fluoren-9-ide.

Figure 2:
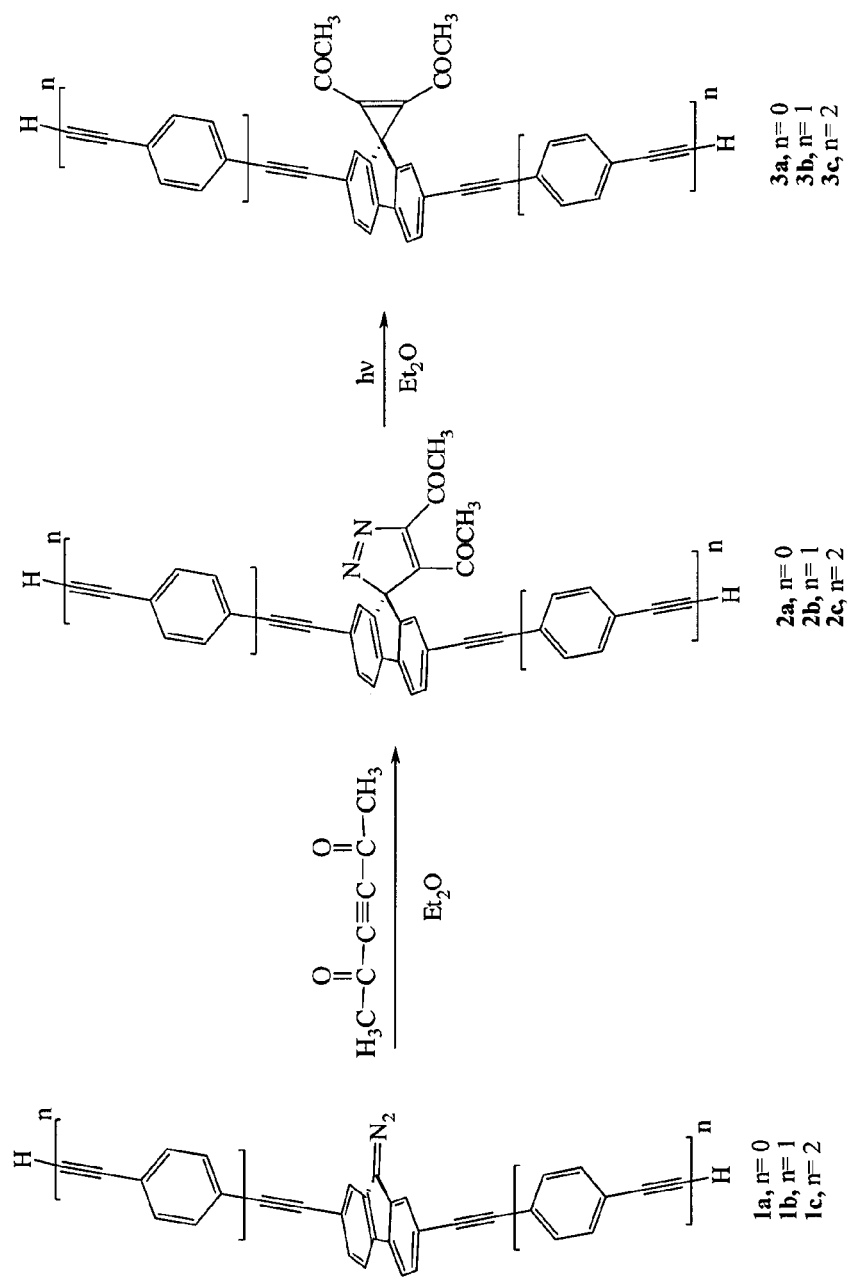
FIG. 2 is a schematic diagram illustrating the preparation of spirocyclopropene precursors 3a-c.

In one exemplary embodiment, the diazo derivatives 1a-c as shown in FIG. 2 are prepared as described in Ahmed et al. and Abdel-Wahab et al. (Ahmed, S. A. Tetrahedron 2009, 65, 1373-1388; Ahmed, S. A.; Khairou, K. S.; Abdel-Wahab, A. A.; Hozien, Z. A.; Dürr, H. Tetrahedron Lett. 2012, 53, 4397-4401; Ahmed, S. A.; Al-Raqa, S. Y.; Moussa, Z.; Hozien, Z. A.; Abdel-Wahab, A. A.; Al-Simaree, A. A.; Al-Amri, S. N.; Soliman, A. S.; Dürr, H. Tetrahedron 2011, 67, 7173-7184—each incorporated by reference herein in its entirety). Referring to FIG. 2, the cycloaddition of hex-3-yne-2,5-dione to the 9-diazofluorene derivatives 1a-c in dry ether in the dark for 24 h led to the formation of the pyrazoles 2a-c in low yields (23%, 29% and 36%, respectively).

In one embodiment, photolysis of the pyrazole derivatives 2a-c was carried out in a Schlenck photochemical reactor made from Pyrex (k>290 nm) (Ahmed, S. A. Tetrahedron 2009, 65, 1373-1388; Ahmed, S. A.; Khairou, K. S.; Abdel-Wahab, A. A.; Hozien, Z. A.; Dürr, H. Tetrahedron Lett. 2012, 53, 4397-4401; Ahmed, S. A.; Al-Raqa, S. Y.; Moussa, Z.; Hozien, Z. A.; Abdel-Wahab, A. A.; Al-Simaree, A. A.; Al-Amri, S. N.; Soliman, A. S.; Dürr, H. Tetrahedron 2011, 67, 7173-7184; Gautron, R. Bull. Soc. Chim. 1968, 3190; Hesse, M.; Meier, H.; Zeeh, B. Spektroskopische Methoden in der Organischen Chemie; Georg Thieme: Stuttgart, New York, 1995; pp 185-186; Schönberg, A. Präparative Organische Photochemie, Chapter 1; Springer: Berlin, 1958—each incorporated by reference herein in its entirety). The source of irradiation was a high-pressure mercury lamp (HPK 125 W, Philips). Solutions to be photolyzed were flushed with dry nitrogen for 30 min before switching on the lamp. Photolysis was performed in dry ether for three hours under a nitrogen atmosphere to give the target diacetyl spirocyclopropene derivatives 3a-c in low yields (29%, 20%, and 14%, respectively) (Gautron, R. Bull. Soc. Chim. 1968, 3190; Hesse, M.; Meier, H.; Zeeh, B. Spektroskopische Methoden in der Organischen Chemie; Georg Thieme: Stuttgart, New York, 1995; pp 185-186; Schönberg, A. Präparative Organische Photochemie, Chapter 1; Springer: Berlin, 1958—each incorporated by reference herein in its entirety.

The structures of the diacetyl spirocyclopropenes 3a-c were established on the basis of analytical and spectroscopic data. For example, in one embodiment, the $^1$H NMR (400 MHz, CDCl$_3$) of the spirocyclopropene precursor 3b showed the following signals: d 7.89 (d, J=1.82 Hz, 2H, CH-arom.), 7.80 (d, J=1.32 Hz, 2H, CH-arom.), 7.55 (d, J=8.9 Hz, 2H, CH-arom.); 7.61 (dd, J=8.9, 2.2 Hz, 4H, CH-arom.), 7.48 (dd, J=8.9, 2.3 Hz, 4H, CH-arom.), 4.02 (s, 2H, CHacetylenic), 2.32 (s, 6H, 2CH$_3$)$^{13}$C NMR (400 MHz, CDCl$_3$) of 3a 182.9 (2C=O), 147.5 (2C), 142.2 (2C), 139.7 (2C), 135.2 (2CH), 132.5 (8CH), 129.8 (2CH), 127.4 (2CH), 123.8 (4C), 122.7 (2C), 95.2 (2C), 90.3 (2C), 83.5 (2C), 81.6 (2CH), 49.8 (C-spiro), 31.1 (2CH$_3$); IR (KBr): m=3028-3092 (C—H, arom.), 2900-2967 (C—H, aliph.), 2252 (acetylenic bond), 1742 (3'-C=O), 1708 (CO—CH$_3$), 1670 (2'-C=O), 1530 (C=C), 1442, 1398, 1278, 1126, 1071, 947, 861, 746 cm$^{-1}$; HR-MS m/e (%) 522.16 [M$^+$] (100.0%), 523.17 (44.4%), 524.17 (16.7%), 525.17 (1.4%) Elemental analysis for 3a (C$_3$9H$_{22}$O$_2$, 522.16): C, 89.63; H, 4.24. Found: C, 89.81; H, 4.14.

Figure 3:
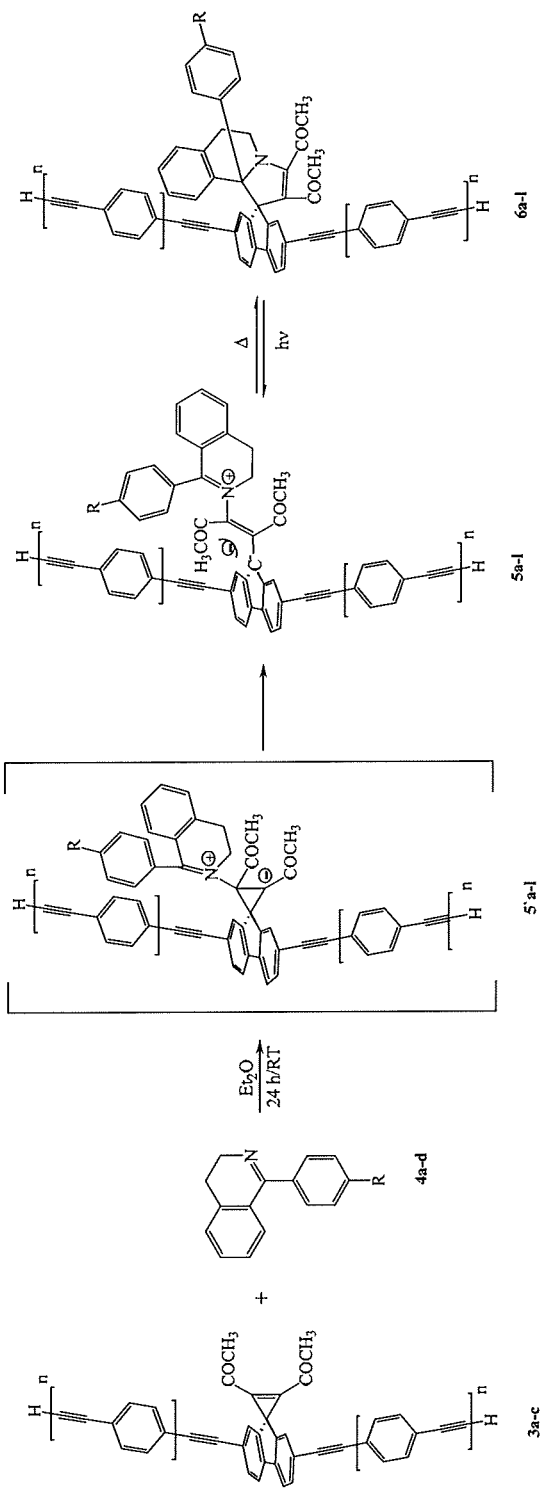
FIG. 3 is a schematic diagram illustrating the preparation of photochromic THIs 6a-l from spirocyclopropenes 3a-c.

Referring to FIG. 3, nucleophilic addition of substituted 1-aryl-3,4-dihydroisoquinolines 4a-d to spirocyclopropene derivatives 3a-c using the cyclopropene route (Dürr, H.; Schommer, C.; Münzmay, T. Angew. Chem. 1986, 25, 565-567; Int. Ed. 1986, 25, 572-574; (b) Dürr, H.; Thome, A.; Kilburg, H.; Bossmann, S.; Blasius, E.; Janzen, K.; Kranz. C. J. Phys. Org. Chem. 1992, 5, 689-698; (c) Dürr, H. Chimica. 1994; 514-515; (d) Dürr, H.; Amlung, M.; Rustemeyer, F.; Tan, Y S.; Deutsche Offenlegungs-Schrift Pat. 1998, 198 349 408; Fromm, R.; Ahmed, S. A.; Hartmann, Th.; Huch, V.; Abdel-Wahab, A. A.; Dürr, H. Eur. J. Org. Chem. 2001, 21, 4077-4080; Weber, C.; Rustemeyer, F.; Dürr, H. Adv. Mater. 1998, 10, 1348-1351; Andreis, C.; Dürr, H.; Wintgens, V.; Valat, P.; Kossanyi, J. Chem. Eur. J. 1997, 3, 509-516; Ahmed, S. A.; Abdel-Wahab, A. A.; Dürr, H. In CRC Handbook of Organic Photochemistry and Photobiology, Chapter 96; Horspool, W. M., Lenci, F., Eds., 2nd ed.; CRC Press: New York, 2003; pp 1-25; Ahmed, S. A.; Hartmann, Th.; Huch, V.; Dürr, H.; Abdel-Wahab, A. A. J. Phys. Org. Chem. 2000, 13, 539-548; Tan, Y.; Ahmed, S. A.; Dürr, H.; Huch, V.; Abdel-Wahab, A. A. Chem. Commun. 2001, 1246-1247; Ahmed, S. A. Mol. Cryst. Liq. Cryst. 2005, 430, 295-300; Ahmed, S. A.; Dürr, H. Mol. Cryst. Liq. Cryst. 2005, 431, 275-280; Ahmed, S. A. Monatsh. Chem. 2004, 135, 1173-1188; Ahmed, S. A.; Abdel-Wahab, A. A.; Dürr, H. J. Photochem. Photobiol. 2003, 154, 131-144; Ahmed, S. A. J. Phys. Org. Chem. 2002, 15, 392-402; Ahmed, S. A. J. Phys. Org. Chem. 2006, 19, 402-414; Ahmed, S. A. J. Phys. Org. Chem. 2007, 20, 564-588; Ahmed, S. A.; Hartmann, Th.; Dürr, H. J. Photochem. Photobiol. 2008, 200, 50-56; Ahmed, S. A.; Pozzo, J. L. J. Photochem. Photobiol. 2008, 200, 57-67; Dürr, H. Chimica 1994, 514-515—each incorporated by reference herein in its entirety), in dry ether at room temperature under a dry nitrogen atmosphere in the absence of light, afforded the novel photochromic tetrahydroindolizines (THIs) 6a-l. The reaction occurred through electrophilic addition of the electrondeficient spirocyclopropene derivatives 3a-c to the nitrogen of the N-heterocyclic isoquinoline derivatives 4a-d, which led to ring-opening via a cyclopropyl-allyl conversion of 50a-l to the colored betaines 5a-l (FIG. 3).

Still referring to FIG. 3, subsequent ring-closure to give THIs 6a-l resulted in a partial slow thermal 1,5-electrocyclization reverse reaction, which can be reversed upon exposure to light. The prepared THIs 6a-l showed low photostability and decomposition can occur during purification and also on standing for a few days at ambient temperature (Fromm, R.; Ahmed, S. A.; Hartmann, Th.; Huch, V.; Abdel-Wahab, A. A.; Dürr, H. Eur. J. Org. Chem. 2001, 21, 4077-4080; Weber, C.; Rustemeyer, F.; Dürr, H. Adv. Mater. 1998, 10, 1348-1351; Ahmed, S. A. Mol. Cryst. Liq. Cryst. 2005, 430, 295-300; Ahmed, S. A.; Dürr, H. Mol. Cryst. Liq. Cryst. 2005, 431, 275-280—each incorporated by reference herein in its entirety).

Figure 4:
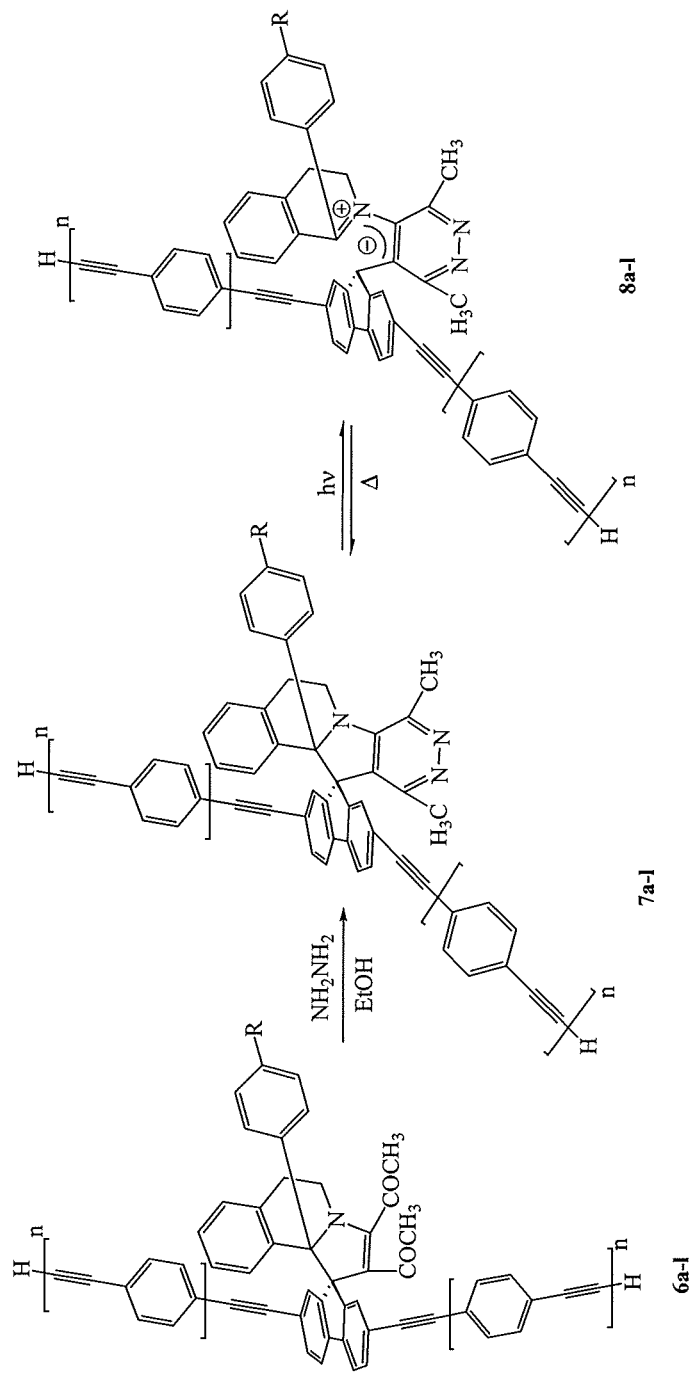
FIG. 4 is a schematic diagram illustrating Method A for the preparation of photochromic THIs 7a-l from THIs 6a-l in ethanol at ambient temperature.

In some embodiments, the decomposition was apparent as a gradual loss of photochromic properties. The THIs 6a-l reach the $t_{30}$ value (a decrease of 30% of the initial absorbance) within the range of 67-92 min depending on both the substituents on the fluorene and isoquinoline moieties. In addition, compared with those THIs bearing ester groups, the THIs in disclosed embodiments herein showed a decrease in the $t_{30}$ values by a factor of 7-9. It was necessary to react them directly after work-up, with hydrazine in absolute ethanol at room temperature for eight hours to afford cis-fixed conjugated photochromic THIs 7a-l shown in FIG. 4. The pure products were obtained as white powders in low to moderate yields (18-52%) after two successive column chromatographic purifications on silica gel using dichloromethane as the eluent.

In an alternative embodiment, a pathway for the synthesis of the target photochromic THIs 7a-l was achieved through palladium-mediated Sonogashira coupling of THIs 9a-d with alkynes 10a-c in the presence of palladium diphenylphosphinedichloride (5%) and CuI/Et$_3$N (Cu$^{2+}$ complex with I=$C_{22}H_{24}N_2O_4$ and Et3N is triethylamine) in dry THF (tetrahydrofuran) to afford the desired photochromic trimethylsilyl THIs 1 1a-l in 23-42% yields after purification by flash chromatography on silica gel with $CH_2Cl_2$ as the eluent. Treatment of THIs 11a-l with tetrabutylammonium fluoride (TBAF) in dry THF for 12 h afforded the desilylated products 6a-l in 39-54% yields.

A Sonogashira reaction is a cross-coupling reaction used in organic synthesis to form carbon-carbon bonds. The reaction employs a palladium catalyst to form a carbon-carbon bond between a terminal alkyne and an aryl or vinyl halide. The Sonogashira cross-coupling reaction can be carried out under mild conditions, for example, at room temperature, in aqueous media. And with a mild base, which has allowed for the use of the reaction in the synthesis of complex molecules.

Figure 5:
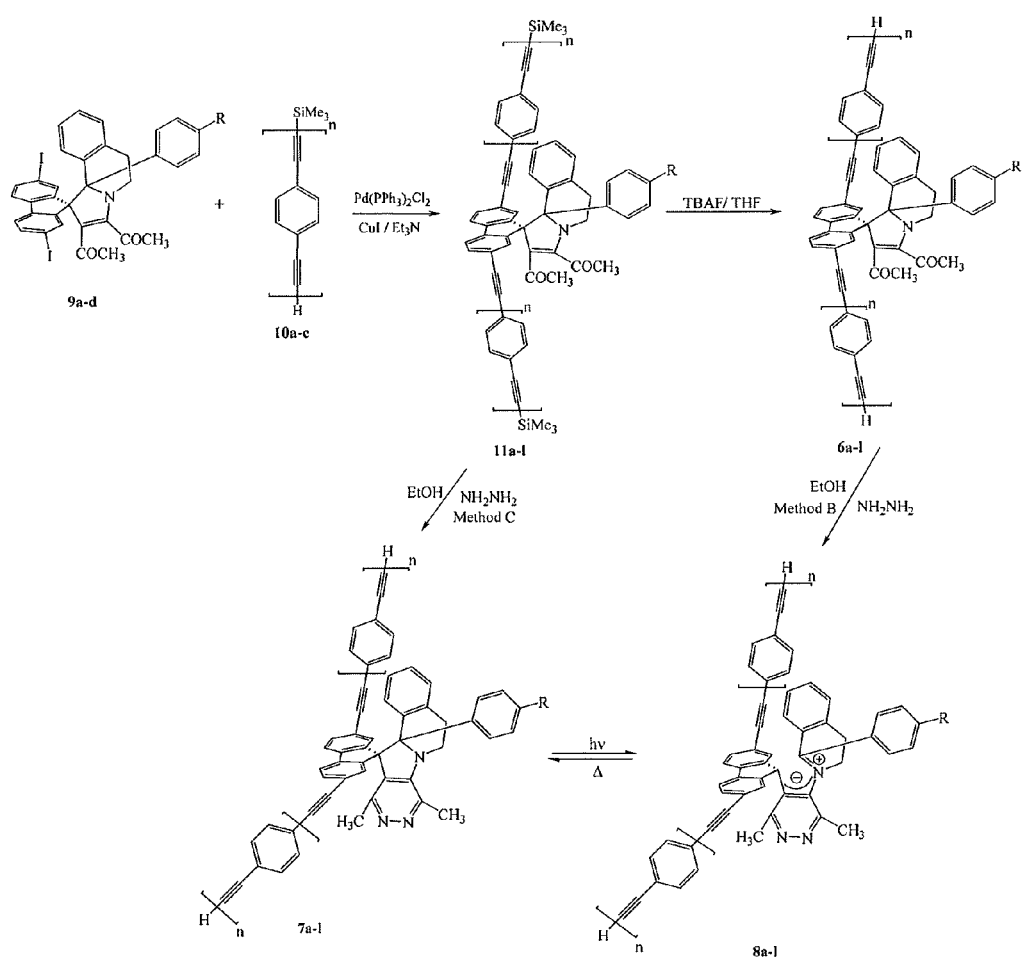
FIG. 5 is a schematic diagram illustrating Methods B and C for preparation of the targets 7a-l and 8a-l.

In another embodiment, rapid treatment of the THIs 6a-l with hydrazine hydrate in absolute ethanol at ambient temperature for eight hours afforded the target THIs 7a-l in 52-68% yields (Method C, FIG. 5).

On the other hand, deprotection of the silyl groups and reactions of the acetyl groups were achieved in one step when photochromic trimethylsilyl THIs 11a-l were treated with hydrazine hydrate in ethanol for six hours to afford the desired THIs 7a-l in 40-51% yields in Method C, as shown in Table 1. Thus, rigid acetylenic bridged THIs 7a-l could be successfully prepared as shown in FIG. 5.

The three products obtained from the different pathways showed the same analytical and spectroscopic data as well as the same melting points and mixed melting points, as shown in Table 1. Table 1 also shows substituent patterns, yields and melting points of the target photochromic THIs 7a-l synthesized by the three alternative methods A-C.

The chemical structures of all the synthesized THIs were confirmed on the bases of spectroscopic and analytical methods. For example the $^1$H NMR (400 MHz, CDCl$_3$) of THI 7k showed the following signals: d 7.93 (d, J=8.1 Hz, 2H, CH-arom.), 7.72 (d, J=1.32 Hz, 2H, CH-arom.), 7.69 (d, J=8.1 Hz, 2H, CH-arom.), 7.63 (d, 7.8, 2H, CH-arom.), 7.62 (dd, J=8.9, 2.2 Hz, 4H, CH-arom.), 7.53 (dd, J=9.9, 2.6 Hz, 4H, CH-arom.), 7.41 (d, J=7.8 Hz, 2H, CH-arom.), 7.37 (dd, J=8.1, 1.9 Hz, 2H, CH-arom.), 7.20 (dd, J=8.1, 1.9 Hz, 2H, CH-arom.), 4.35 (s, 2H, acetylenic CH); 3.44 (t, J=2.3 Hz, 2H, CH$_2$), 2.95 (t, J=2.3 Hz, 2H, CH$_2$); 2.40 (s, 3H, CH3); 1.39 (s, 3H, CH$_3$) ppm; $^{13}$C NMR (400 MHz, CDCl3) of THI 7k showed the following signals: d 158.2 (C); 146.20 (C); 144.9 (C); 143.4 (C); 142.2 (2C); 141.0 (2C); 119.2 (C); 135.9 (C); 135.7 (C); 134.3 (2CH); 132.7 (2CH); 130.9 (9CH); 129.4 (2CH); 128.3 (2CH); 127.8 (2CH); 126.9 (2CH); 125.8 (2CH); 122.7 (4C); 121.5 (2C); 119.4 (2C); 92.5 (2C); 88.9 (2C); 86.0 (C); 82.7 (2C); 80.4 (2CH); 46.4 (CH2); 31.9 (CH2); 21.7 (CH3); 19.7 (CH3); IR (KBr): m=3030-3059 (C—H, arom.), 2965-2998 (C—H, aliph.), 2242 (acetylenic bond), 2215 (CN), 1741 (3'-C=O), 1712 (CO—CH3), 1687 (2'-C=O), 1637 (C=N), 1523 (C=C), 1421, 1387, 1282, 1174, 1071, 938, 874, 758 cm$^{-1}$; HR-MS m/e (%) 750.28 [M$^+$] (100.0%), 750.28 (61.7%), 750.22 (18.1%), 753.20 (2.9%); Elemental analysis for THI 7k ($C_{55}H_{34}N_4$): C, 87.97; H, 4.56; N, 7.46. Found: C, 87.69; H, 4.62; N, 7.31.

TABLE 1

| THI | X | n | Method | Yield (%) | mp (° C.) |
|---|---|---|---|---|---|
| 7a | H | 0 | A | 24 | 191 |
| 7a | H | 0 | B | 28 | 192-193 |
| 7a | H | 0 | C | 46 | 192 |
| 7b | H | 1 | A | 28 | 180 |
| 7b | H | 1 | B | 33 | 182 |
| 7b | H | 1 | C | 47 | 181-182 |
| 7c | H | 2 | A | 20 | 166-168 |
| 7c | H | 2 | B | 30 | 165-167 |
| 7c | H | 2 | C | 50 | 166-167 |
| 7d | CH$_3$ | 0 | A | 18 | 146 |
| 7d | CH$_3$ | 0 | B | 23 | 145-146 |
| 7d | CH$_3$ | 0 | C | 41 | 147 |
| 7e | CH$_3$ | 1 | A | 29 | 136 |
| 7e | CH$_3$ | 1 | B | 31 | 133-135 |
| 7e | CH$_3$ | 1 | C | 40 | 134 |
| 7f | CH$_3$ | 2 | A | 30 | 119 |
| 7f | CH$_3$ | 2 | B | 34 | 121 |
| 7f | CH$_3$ | 2 | C | 51 | 120 |
| 7g | F | 0 | A | 44 | 172 |
| 7g | F | 0 | B | 32 | 173 |
| 7g | F | 0 | C | 48 | 172 |
| 7h | F | 1 | A | 41 | 165 |
| 7h | F | 1 | B | 29 | 164-165 |
| 7h | F | 1 | C | 46 | 166 |
| 7i | F | 2 | A | 46 | 153 |
| 7i | F | 2 | B | 33 | 153 |
| 7i | F | 2 | C | 44 | 152 |
| 7j | CN | 0 | A | 52 | 211 |
| 7j | CN | 0 | B | 34 | 210 |
| 7j | CN | 0 | C | 49 | 209 |
| 7k | CN | 1 | A | 49 | 191 |
| 7k | CN | 1 | B | 33 | 190-191 |
| 7k | CN | 1 | C | 40 | 192 |
| 7l | CN | 2 | A | 48 | 179 |
| 7l | CN | 2 | B | 27 | 178 |
| 7l | CN | 2 | C | 43 | 177-178 |

Figure 6:
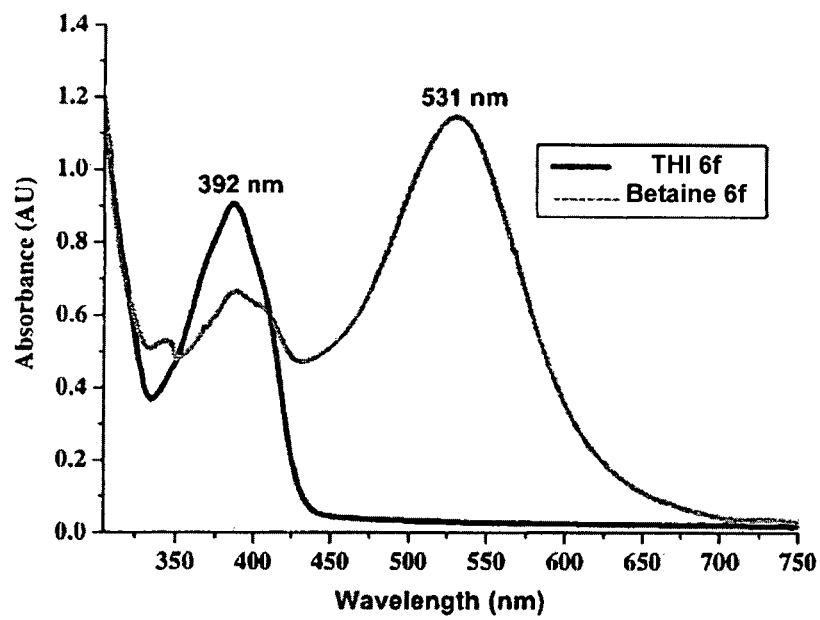
FIG. 6 is a UV-vis spectra of photochromic THI 6f and the corresponding betaine 5f in dichloromethane at ambient temperature ($c=1\times10^{-5}$ mol/L).
Figure 7:
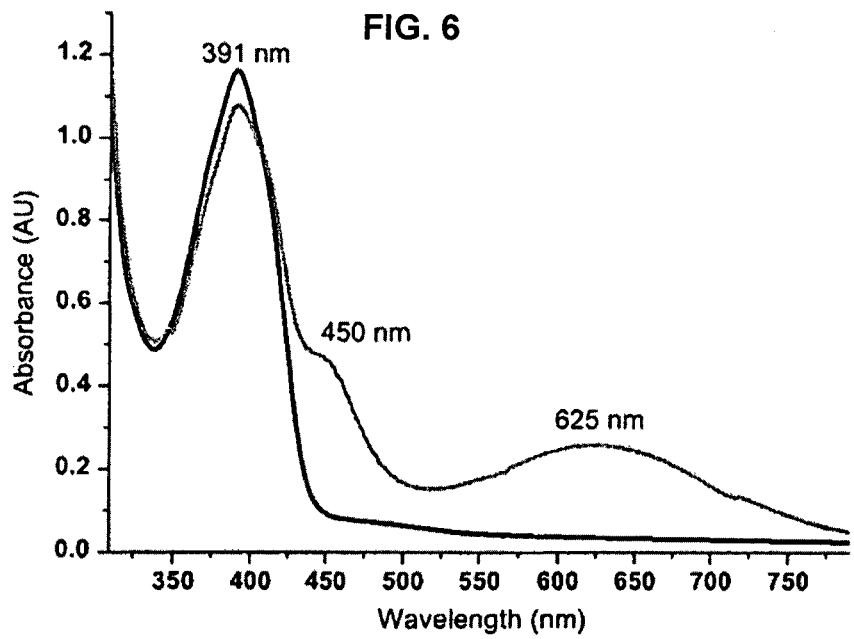
FIG. 7 is a UV-vis spectra of photochromic THI 7j at ambient temperature and the corresponding betaine 8j at $-30°$ C. in dichloromethane ($c=1\times10^{-5}$ mol/L).

In one embodiment, the electronic spectra of the newly synthesized THIs 6a-l and 7a-l were measured in dichloromethane at a concentration of 1×10$^{-5}$ mol/L at 23° C. using a UV-vis spectrophotometer. All the THIs showed yellow color in both the solid state and in dichloromethane (Table 2). Table 2 summarizes absorption spectral data of THIs 6a-l and 7a-l and their corresponding betaines 5a-l and 8a-l, and their kinetic data (monitored by UV-vis-spectrophotometry at ambient temperature for betaines 5a-l and at −30° C. for betaines 8a-l) in CH$_2$Cl$_2$ at a concentration of 1×10$^{-5}$ mol/L. The intensities (log ϵ) of these bands were found to be between 4.01 and 4.46 depending on the number of alkyne groups and substitution on the isoquinoline moiety. As depicted in FIGS. 6, 7 and Table 2, the absorptions of THIs 6a-l and 7a-l were observed in the far UV-region and showed absorption maxima between 387 and 395 nm. This absorption is dependent on the number of phenylethyne (n) substituents on the fluorene (region A). As established previously (Ahmed, S. A.; Hartmann, Th.; Dürr, H. J. Photochem. Photobiol. 2008, 200, 50-56; Ahmed, S. A.; Pozzo, J. L. J. Photochem. Photobiol. 2008, 200, 57-67; Dürr, H. Chimica 1994, 514-515; Masson, J.-F.; Hartmann, Th.; Dürr, H.; Booksh, K. S. Opt. Mater. 2004, 27, 435-439; Terazono, Y.; Kodis, J.; Andreasson, J.; Jeong, G.; Brune, A.; Hartmann, Th.; Dürr, H.; Moore, A. L.; Moore, Th. M.; Gust, D. J. Phys. Chem. 2004, 108, 1812-1814; Shrestha, T. B.; Melin, J.; Liu, Y.; Dolgounitcheva, O.; Zakrzewski, V. G.; Pokhrel, M. R.; Gogritchiani, E.; Ortiz, J. V.; Turro, C.; Bossmann, S. H. Photochem. Photobiol. Sci. 2008, 7, 1449-1456; Shrestha, T. B.; Kalita, M.; Pokhrel, M. J.; Liu, Y.; Troyer, D. L.; Turro, C.; Bossmann, S. H.; Dürr, H. J. Org. Chem. 2013, 78, 1903-1909; Gogritchiani, E.; Hartmann, Th.; Palm, B.; Samsoniya, Sh.; Dürr, H. J. Photochem. Photobiol., B 2002, 67, 18-22; Ahmed, S. A. Tetrahedron 2009, 65, 1373-1388; Ahmed, S. A.; Khairou, K. S.; Abdel-Wahab, A. A.; Hozien, Z. A.; Dürr, H. Tetrahedron Lett. 2012, 53, 4397-4401; Ahmed, S. A.; Al-Raqa, S. Y.; Moussa, Z.; Hozien, Z. A.; Abdel-Wahab, A. A.; Al-Simaree, A. A.; Al-Amri, S. N.; Soliman, A. S.; Dürr, H. Tetrahedron 2011, 67, 7173-7184; Gautron, R. Bull. Soc. Chim. 1968, 3190; Hesse, M.; Meier, H.; Zeeh, B. Spektroskopische Methoden in der Organischen Chemie; Georg Thieme: Stuttgart, New York, 1995; pp 185-186; Schönberg, A. Präparative Organische Photochemie, Chapter 1; Springer: Berlin, 1958—each incorporated by reference herein in its entirety), these absorption bands can be assigned to the locally excited π-π*-transition (LE) located in the butadienyl-vinyl-amine chromophores (Shrestha, T. B.; Kalita, M.; Pokhrel, M. J.; Liu, Y.; Troyer, D. L.; Turro, C.; Bossmann, S. H.; Dürr, H. J. Org. Chem. 2013, 78, 1903-1909; Gogritchiani, E.; Hartmann, Th.; Palm, B.; Samsoniya, Sh.; Dürr, H. J. Photochem. Photobiol., B 2002, 67, 18-22; Ahmed, S. A. Tetrahedron 2009, 65, 1373-1388; Ahmed, S. A.; Khairou, K. S.; Abdel-Wahab, A. A.; Hozien, Z. A.; Dürr, H. Tetrahedron Lett. 2012, 53, 4397-4401; Ahmed, S. A.; Al-Raqa, S. Y.; Moussa, Z.; Hozien, Z. A.; Abdel-Wahab, A. A.; Al-Simaree, A. A.; Al-Amri, S. N.; Soliman, A. S.; Dürr, H. Tetrahedron 2011, 67, 7173-7184; Gautron, R. Bull. Soc. Chim. 1968, 3190; Hesse, M.; Meier, H.; Zeeh, B. Spektroskopische Methoden in der Organischen Chemie; Georg Thieme: Stuttgart, New York, 1995; pp 185-186; Schönberg, A. Präparative Organische Photochemie, Chapter 1; Springer: Berlin, 1958—each incorporated by reference herein in its entirety) of the THIs 6a-l and 7a-l (Table 2).

TABLE 2

| THI/Betaine | $\lambda_{max}$(THI) [nm] | $\lambda_{max}$(betaine) [nm] | Color of betaine | $t_{1/2}(s)$ Betaine |
|---|---|---|---|---|
| 6a/5a | 389 | 528 | red | 210 |
| 6b/5b | 388 | 532 | red | 235 |
| 6c/5c | 395 | 536 | red-violet | 246 |
| 6d/5d | 387 | 526 | red | 1245 |
| 6e/5e | 386 | 528 | red | 1394 |
| 6f/5f | 392 | 531 | red | 1463 |
| 6g/5g | 394 | 533 | red | 968 |
| 6h/5h | 389 | 538 | red-violet | 1007 |
| 6i/5i | 390 | 537 | red-violet | 1120 |
| 6j/5j | 391 | 542 | red-violet | 1369 |
| 6k/5k | 394 | 544 | red-violet | 1527 |
| 6l/5l | 395 | 545 | red-violet | 1798 |
| 7a/8a | 386 | 443, 628 | blue | 30 |
| 7b/8b | 387 | 446, 630 | blue | 37 |
| 7c/8c | 398 | 447, 630 | blue | 46 |
| 7d/8d | 385 | 346, 638 | blue | 96 |
| 7e/8e | 386 | 346, 640 | blue | 106 |
| 7f/8f | 386 | 447, 650 | blue-green | 117 |
| 7g/8g | 385 | 440, 623 | blue | 79 |
| 7h/8h | 356 | 441, 628 | blue | 88 |
| 7i/8i | 388 | 441, 630 | blue | 97 |
| 7j/8j | 391 | 450, 625 | blue | 119 |
| 7k/8k | 391 | 448, 628 | blue | 102 |
| 7l/8l | 392 | 443, 632 | blue | 130 |

Irradiation of THIs 6a-l with ultraviolet light for two minutes with an approximate 7 cm distance between the light and the probe, led to ring-opened betaines 5a-l (see FIG. 6). The colored betaine forms 5a-l varied from red to red-violet in $CH_2Cl_2$ (concentration of $1\times10^{-5}$ mol/L) at room temperature because of their slower 1,5-electrocyclization, which refers to the stabilization of the charged zwitterionic betaines. All the absorption maxima of the colored betaines 5a-l were found to be in the visible region and lie between 528 (betaines 5a,e) and 545 nm (betaine 5l). The UV-vis spectra of the colored betaines containing a cyano-substituted isoquinoline, as in THIs 5j-l, exhibit a red-violet color and were shifted bathochromically by about 17 nm compared with non-substituted betaine 5a. This can be attributed to the electron-attracting property of the cyano group.

Furthermore, a noticeable bathochromic shift of about 2-6 nm was observed upon increasing the number of bridged phenyl acetylenic groups from n=0 to n=3, with no dependency on the substituted or non-substituted isoquinoline moiety. This may be attributed to the increasing aromaticity of the fluorene unit conjugated with the aromatic phenyl rings through the bridged acetylenic bond. Additional spectroscopic data on the UV-vis measurements of the colored betaines under investigation are listed in Table 2.

Figure 8:
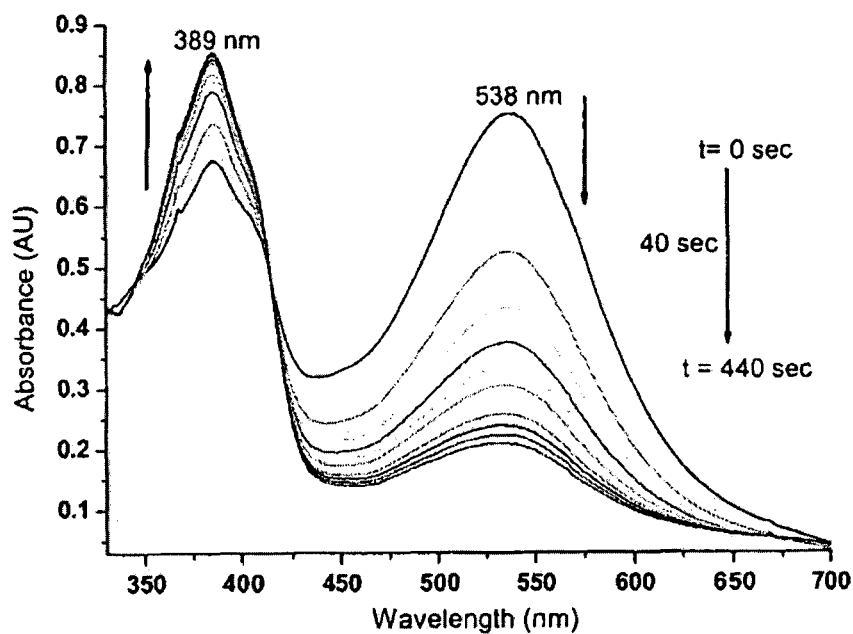
FIG. 8 is a graph showing kinetics of the thermal fading of the 1,5-electrocyclization of betaine 6h to THI 5h (cycle time=40 s, and run time=440 s) in $CH_2Cl_2$ ($c=1\times10^{-5}$ mol/L) at $25°$ C.

On the other hand, irradiation of the target THIs 7a-l at ambient temperature did not afford the colored betaines 8a-l, and no photochromic properties were evident. This can be attributed to the 1,5-electrocyclic reaction to THIs 7a-l. This phenomenon motivated the inventors of this present disclosure to study further the conditions for obtaining the photochromic properties of this class of THI system. Thus, the colored betaines 8a-l were analyzed using an FT-UV-vis photospectrometer after irradiation of the THIs 7a-l at low temperature (−30° C.). As shown in FIG. 7, The blue to blue-green colored betaines showed two absorption maxima around 440-450 and 620-750 nm depending on the substitutents on both fluorene and isoquinoline regions. In FIG. 8, the kinetics of the thermal 1,5-electrocyclization of betaines 5a-l were studied by using multichannel FT-UV-vis spectrophotometry. The kinetic measurements showed that the half-lives of the colored betaines 5a-l were in the second domain between 210 and 1798 s (see Table 2, FIG. 8).

In one embodiment, a highly pronounced increase in the half-lives of the betaines with a methyl substituted isoquinoline (5d,e,f) by approximately a factor of six was observed compared with the half-lives of the betaines 5a-c bearing a non-substituted isoquinoline. This increase in the half-lives may be attributed to the stabilization of the electrostatic charges on the betaines by the electron-donating methyl group.

Figure 9:
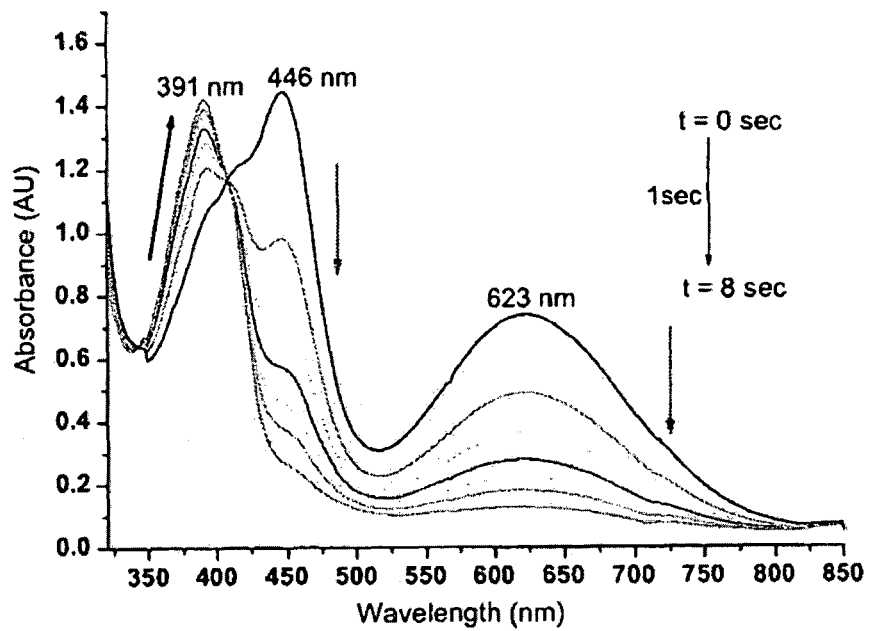
FIG. 9 is a graph showing FT-UV-vis kinetics of the thermal fading of the 1,5-electrocyclization of betaine 8e to THI 7e (cycle time=1 s, and run time=8 s) in $CH_2Cl_2$ ($c=1\times10^{-5}$ mol/L) at $-30°$ C.
Figure 10:
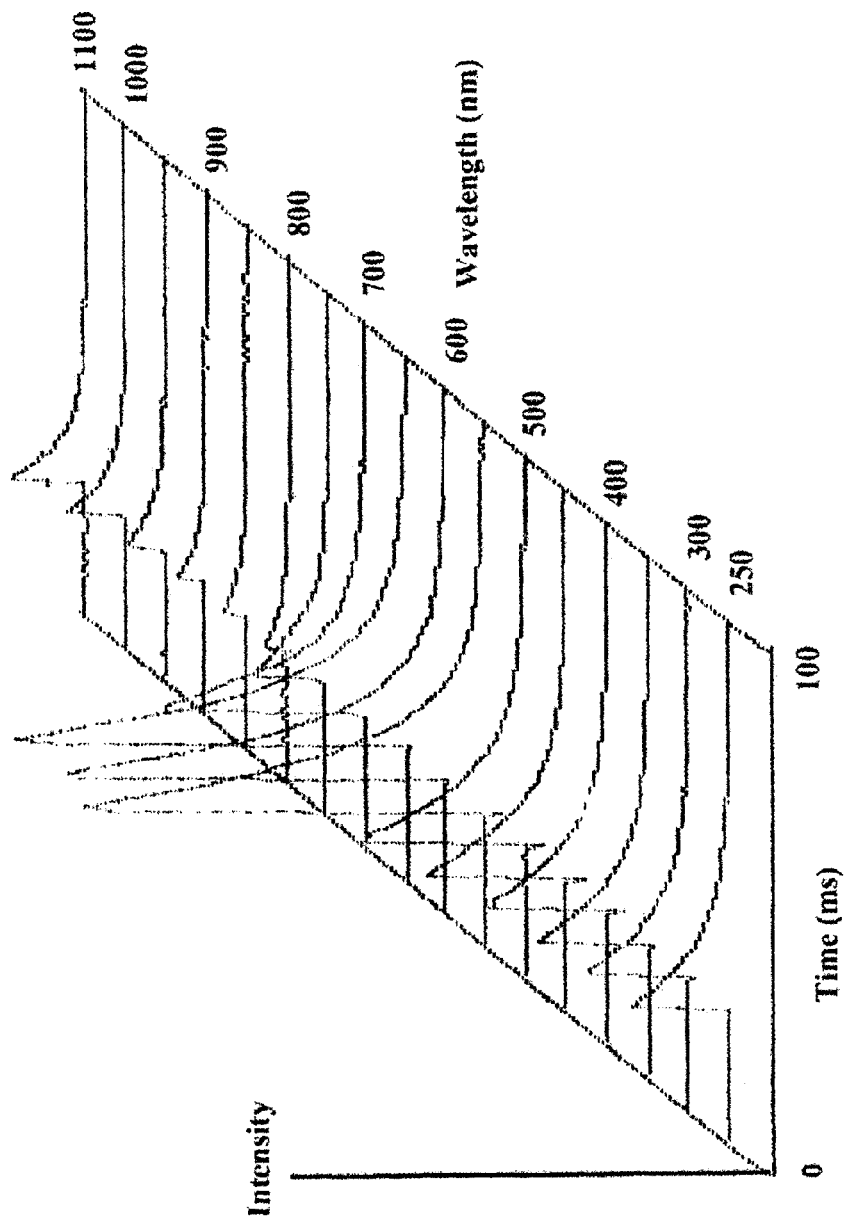
FIG. 10 is a graph showing flash photolysis of THI 7f for determination of the absorption maxima and half-life time of betaine 8f in dichloromethane at $23°$ C. ($c=1\times10^{-5}$ mol/L).

In one embodiment, an increase in the half-lives of the betaines by increasing the number acetylenic bridges from one to three in the fluorene part was recorded. This may be attributed to the bulky sterically hindered phenyl rings substituted on the fluorene moiety. On the other hand, low temperature FT-UV-vis (−30° C.) and flash photolysis techniques were used for detection of both the absorption maxima and the half-lives of the betaine forms 8a-l (see FIGS. 9, 10). The half lives were found to be in the millisecond domain and were between 30-130 ms. The rapid 1,5-electrocyclization suggested that the betaine structure exists only in a cis-fixed form and cyclized back thermally from this form to the THI skeleton. The pronounced tuning of the absorption maxima and the kinetic properties by changing the substitution in the fluorene region, as well as in the dihydroisoquinoline region, provides a means to utilize these compounds in many applications, particularly in the area of molecular electronics.

A variety of photochromic tetrahydroindolizines (THIs) were synthesized via Sonogashira coupling reactions. The coupling reactions between fluorenes (region A) and acetylenic bridges in addition to substitution on the dihydroisoquinolines (region B) resulted in target molecules with extended photochromism. Interesting photochromic properties have been observed by tuning the chemical structure of the photochromic THI by varying the number of acetylenic bridges in the fluorene part between 0 and 2 and the substitution on the isoquinoline region. This pronounced influence of the substituents in both regions A and C showed strong effects on the UV-vis absorptions of DHIs and betaines, as well as their kinetic properties (half-lives). The cis-fixed betaine forms with 1,5-electrocyclization were confirmed using FT-UV-vis and flash photolysis measurements. These broad spectrum photochromic properties of the novel THIs and their corresponding betaines should aid in finding suitable applications in the field of electronic devices, molecular electronics, optoelectronics, nonlinear optics, computer ships, nanotechnology and polymeric thin film applications. Photochromic THIs are regarded as better candidates for optical storage media electronic devices applications than other classes of photochromic compounds. Photochromic THIs display a high efficiency of photoisomerizations, that is the 1,5-electrocyclization between two distinct isomeric states: ring-opening form (betaine-form) and ring closed form (THI-form), sufficient thermal stability of both the open and the close forms, a very high resistance to photofatigue, and the ease with which the reaction can be monitored by UV/vis spectroscopy.

In one embodiment, any one of or a combination of the photochromic tetrahydrolizine compounds disclosed in the present invention may be utilized as molecular switches in a photoswitch electronic device. Components of a photoswitch electronic device include, for example, photoresistor, phototransistor, photosensor, photodetector, photodiode, optical detector.

In one embodiment, the photoswitch device consists of at least one photosensor component wherein a photochromic composition is contained within a housing. The photochromic composition is made up of one or more of the photochromic tetrahydrolizine compounds disclosed herein and optionally, metals and one or more other types of photochromic compounds (organic and inorganic). Constructive materials for the housing are polymers such as of liquid crystal materials, self-assembling materials, polyacrylates, polymethacrylates, poly($C_1$-$C_{12}$ alkyl methacrylates). polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyamide, polyimide, polyurethane, poly(urea)urethane, polythiourethane, polythio(urea)urethane, polycyclic alkene, polyurethanes, poly(ethylene terephthalate), polyolefin, polystyrene, poly(alpha methylstyrene), copoly(styrene-methylmethacrylate), copoly(styrene acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers, copolymers thereof, and/or mixtures thereof.

In one embodiment, the photosensor in the photoswitch device is connected to a circuit that is assembled on a printed circuit board or a common board. Other components of the circuit include a potentiometer that adjusts the level of light sensitivity or input, a relay, a resistor and one or more transistors.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A compound represented by at least one of the Formulas I-IV:

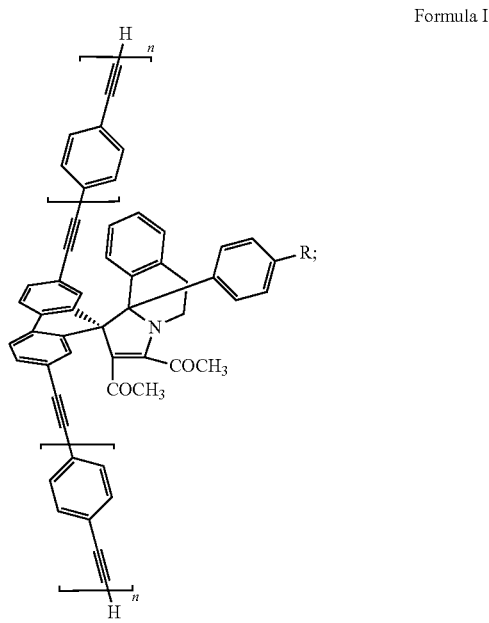

Formula I

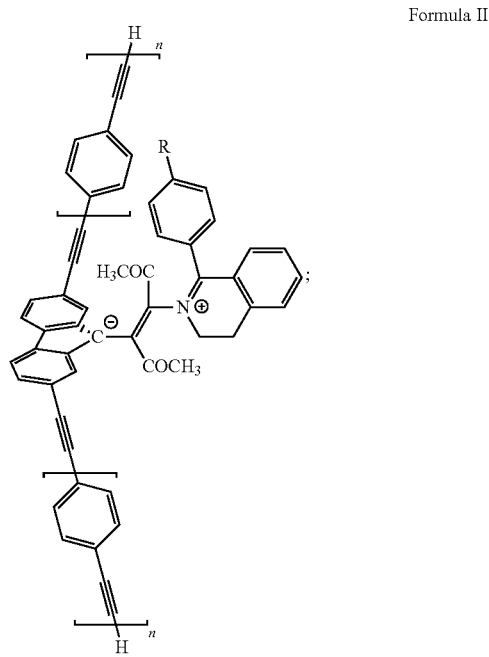

Formula II

-continued

Formula III

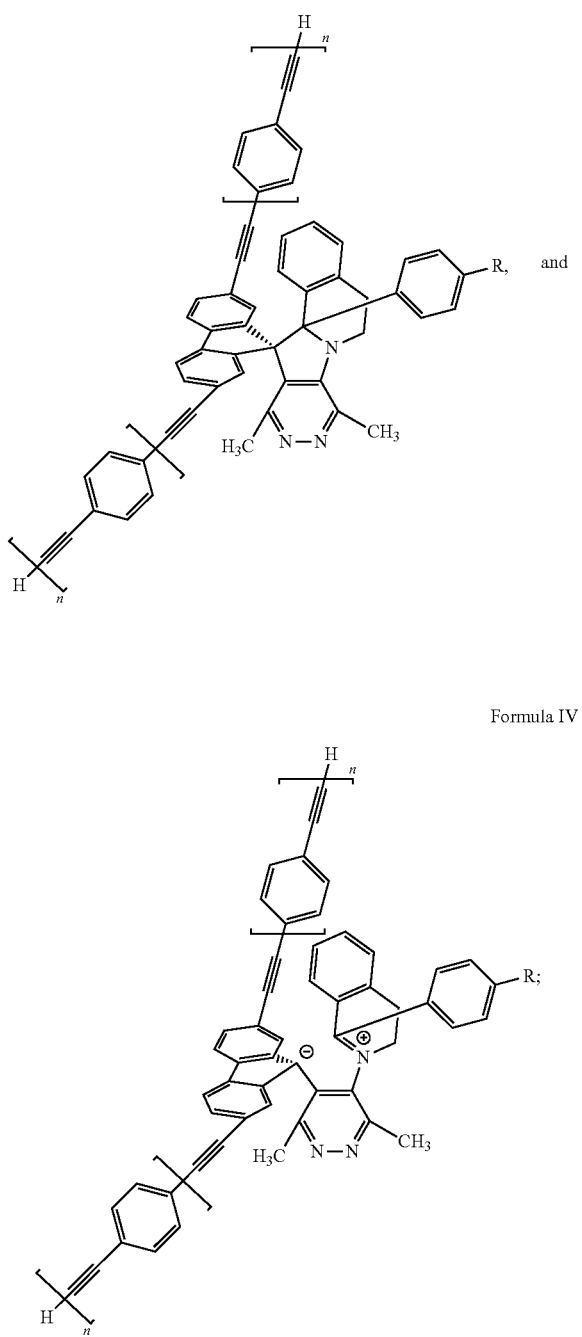

Formula IV wherein:
n is an integer selected from the group consisting of 0, 1, and 2; and
R is selected from the group consisting of hydrogen, alkyl, alkenyl, aryl, arylakyl, acyloxy, heteroaryl, amino, acylamino, alkylamino, acyl, hydroxy, alkoxy, halo, and cyano.

2. The compound of claim 1, wherein said compound is selected from the group consisting of:

1-((2'S,10b'R)-2'-methyl-10b'-phenethyl-3',5',6',10b'-tetrahydro-2'H-spiro[fluorene-9, 1'-pyrrolo[2,1-a]isoquinolin]-3'-yl)ethanone;
1-((2'S, 10b'R)-2'-methyl-10b'-(4-m ethylphenethyl)-3',5', 6',10b'-tetrahydro-2'H-spiro[fluorene-9,1'-pyrrolo[2,1-a]isoquinolin]-3'-yl)ethanone;
1-((2'S,10b'R)-10b'-(4-fluorophenethyl)-2'-methyl-3',5', 6',10b'-tetrahydro-2'H-spiro[fluorene-9,1'-pyrrolo[2,1-a]isoquinolin]-3'-yl)ethanone;
4-(2-((2'S,10b'R)-3'-acetyl-2'-methyl-3',5',6',10b'-tetrahydro-2'H-spiro[fluorene-9, 1'-pyrrolo[2,1-a]isoquinoline]-10b'-yl)ethyl)benzonitrile;
1-((2'S,10b'R)-2'-methyl-10b'-phenethyl-2,7-diphenyl-3', 5',6' 10b'-tetrahydro-2'H-spiro[fluorene-9,1'-pyrrolo[2, 1-a]isoquinolin]-3'-yl)ethanone;
1-((2'S,10b'R)-2'-methyl-10b'-(4-methylphenethyl)-2, 7-diphenyl-3',5',6',10b'-tetrahydro-2'H-spiro[fluorene-9,1'-pyrrolo[2,1-a]isoquinolin]-3'-yl)ethanone;
1-((2'S,10b'R)-10b'-(4-fluorophenethyl)-2'-methyl-2,7-diphenyl-3',5',6',10b'-tetrahydro-2'H-spiro[fluorene-9, 1'-pyrrolo[2,1-a]isoquinolin]-3'-yl)ethanone;
4-(2-((2'S,10b'R)-3'-acetyl-2'-methyl-2,7-diphenyl-3',5, 6',10b'-tetrahydro-2'H-spiro[fluorene-9,1'-pyrrolo[2,1-a]isoquinoline]-10b'-yl)ethyl)benzonitrile;
1-((2'S,10b'R)-2'-methyl-10b'-phenethyl-2,3,6,7-tetraphenyl-3',5',6' 10b'-tetrahydro-2'H-spiro[fluorene-9,1'-pyrrolo[2,1-a]isoquinolin]-3'-yl)ethanone;
1-((2'S,10b'R)-2'-methyl-10b'-(4-methylphenethyl)-2,3,6, 7-tetraphenyl-3',5',6',10b'-tetrahydro-2'H-spiro[fluorene-9,1'-pyrrolo[2,1-a]isoquinolin]-3'-yl)ethanone;
1-((2'S, 10b'R)-2'-methyl-10b'-(4-methylphenethyl)-2, 3,6,7-tetraphenyl-3',5',6',10b'-tetrahydro-2'H-spiro[fluorene-9,1'-pyrrolo[2,1-a]isoquinolin]-3'-yl)ethanone;
1-((2'S,10b'R)-2'-methyl-10b'-(4-methylphenethyl)-2, 3,6,7-tetraphenyl-3',5',6',10b'-tetrahydro-2'H-spiro[fluorene-9,1'-pyrrolo[2,1-a]isoquinolin]-3'-yl)ethanone;
(Z)-9-(2,5-dioxo-4-(1-phenyl-3,4-dihydroisoquinolin-2-ium-2-yl)hex-3-en-3-yl)-9H-fluoren-9-ide;
(Z)-9-(2,5-di oxo-4-(1-(p-tolyl)-3,4-dihydroisoquinolin-2-ium-2-yl)hex-3-en-3-yl)-9H-fluoren-9-ide;
(Z)-9-(4-(1-(4-fluorophenyl)-3,4-dihydroisoquinolin-2-ium-2-yl)-2, 5-dioxohex-3-en-3-yl)-9H-fluoren-9-ide;
(Z)-9-(4-(1-(4-cyanophenyl)-3,4-dihydroisoquinolin-2-ium-2-yl)-2, 5-dioxohex-3-en-3-yl)-9H-fluoren-9-ide;
(Z)-9-(2,5-dioxo-4-(1-phenyl-3,4-dihydroisoquinolin-2-ium-2-yl)hex-3-en-3-yl)-2,7-diphenyl-9H-fluoren-9-ide;
(Z)-9-(2,5-dioxo-4-(1-(p-tolyl)-3,4-dihydroisoquinolin-2-ium-2-yl)hex-3-en-3-yl)-2,7-diphenyl-9H-fluoren-9-ide;
(Z)-9-(4-(1-(4-fluorophenyl)-3,4-dihydroisoquinolin-2-ium-2-yl)-2, 5-dioxohex-3-en-3-yl)-2,7-diphenyl-9H-fluoren-9-ide;
(Z)-9-(4-(1-(4-cyanophenyl)-3,4-dihydroisoquinolin-2-ium-2-yl)-2, 5-dioxohex-3-en-3-yl)-2,7-diphenyl-9H-fluoren-9-ide;
(Z)-9-(2,5-dioxo-4-(1-phenyl-3,4-dihydroisoquinolin-2-ium-2-yl)hex-3-en-3-yl)-2,3,6,7-tetraphenyl-9H-fluoren-9-ide;
(Z)-9-(2,5-dioxo-4-(1-(p-tolyl)-3,4-dihydroisoquinolin-2-ium-2-yl)hex-3-en-3-yl)-2,3,6,7-tetraphenyl-9H-fluoren-9-ide;
(Z)-9-(4-(1-(4-fluorophenyl)-3,4-dihydroisoquinolin-2-ium-2-yl)-2, 5-dioxohex-3-en-3-yl)-2,3,6,7-tetraphenyl-9H-fluoren-9-ide;

(Z)-9-(4-(1-(4-cyanophenyl)-3,4-dihydroisoquinolin-2-ium-2-yl)-2, 5-dioxohex-3-en-3-yl)-2,3,6,7-tetraphenyl-9H-fluoren-9-ide;
8',11'-dimethyl-12a'-phenethyl-6',12a'-dihydro-5'H-spiro [fluorene-9,12'-pyridazino[4',5':4,5]pyrrolo[2,1-a]isoquinoline];
8',11'-dimethyl-12a'-(4-methylphenethyl)-6',12a'-dihydro-5'H-spiro[fluorene-9,12'-pyridazino[4',5':4,5]pyrrolo[2,1-a]isoquinoline];
12a'-(4-fluorophenethyl)-8',11'-dimethyl-6',12a'-dihydro-5'H-spiro[fluorene-9,12'-pyridazino[4',5':4,5]pyrrolo[2,1-a]isoquinoline];
4-(2-(8',11'-dimethyl-6',12a'-dihydro-5'H-spiro[fluorene-9,12'-pyridazino[4',5':4,5]pyrrolo[2,1-a]isoquinolin]-12a'-yl)ethyl)benzonitrile;
8',11'-dimethyl-12a'-phenethyl-2,7-diphenyl-6',12a'-dihydro-5'H-spiro[fluorene-9,12'-pyridazino[4',5':4,5]pyrrolo[2,1-a]isoquinoline];
8',1'-dimethyl-12a'-(4-methylphenethyl)-2,7-diphenyl-6',12a'-dihydro-5'H-spiro[fluorene-9,12'-pyridazino[4',5':4, 5]pyrrolo[2,1-a]isoquinoline]
12a'-(4-fluorophenethyl)-8',11'-dimethyl-2,7-diphenyl-6',12a'-dihydro-5'H-spiro[fluorene-9,12'-pyridazino[4',5':4,5]pyrrolo[2,1-a]isoquinoline];
4-(2-(8',11'-dimethyl-2,7-diphenyl-6',12a'-dihydro-5'H-spiro[fluorene-9,12'-pyridazino[4',5':4,5]pyrrolo[2,1-a]isoquinolin]-12a'-yl)ethyl)benzonitrile'
8',11'-dimethyl-12a'-phenethyl-2,3,6,7-tetraphenyl-6',12a'-dihydro-5'H-spiro[fluorene-9,12'-pyridazino[4',5':4,5]pyrrolo[2,1-a]isoquinoline];
8',11'-dimethyl-12a'-(4-methylphenethyl)-2,3,6,7-tetraphenyl-6',12a'-dihydro-5'H-spiro[fluorene-9,12'-pyridazino[4',5':4, 5]pyrrolo[2,1-a]isoquinoline];
12a'-(4-fluorophenethyl)-8',11'-dimethyl-2,3,6,7-tetraphenyl-6',12a'-dihydro-5'H-spiro[fluorene-9,12'-pyridazino[4',5':4,5]pyrrolo[2,1-a]isoquinoline];
4-(2-(8',11'-dimethyl-2,3,6,7-tetraphenyl-6',12a'-dihydro-5'H-spiro[fluorene-9,12'-pyridazino[4',5':4,5]pyrrolo[2,1-a]isoquinolin]-12a'-yl)ethyl)benzonitrile;
9-(3,6-dimethyl-5-(1-phenethyl-3,4-dihydroisoquinolin-2-ium-2-yl)pyridazin-4-yl)-9H-fluoren-9-ide;
9-(3,6-dimethyl-5-(1-(4-methylphenethyl)-3,4-dihydroisoquinolin-2-ium-2-yl)pyridazin-4-yl)-9H-fluoren-9-ide;
9-(5-(1-(4-fluorophenethyl)-3,4-dihydroisoquinolin-2-ium-2-yl)-3,6-dimethylpyridazin-4-yl)-9H-fluoren-9-ide;
9-(5-(1-(4-cyanophenethyl)-3,4-dihydroisoquinolin-2-ium-2-yl)-3,6-dimethylpyridazin-4-yl)-9H-fluoren-9-ide;
9-(3,6-dimethyl-5-(1-phenethyl-3,4-dihydroisoquinolin-2-ium-2-yl)pyridazin-4-yl)-2,7-diphenyl-9H-fluoren-9-ide;
9-(3,6-dimethyl-5-(1-(4-methylphenethyl)-3,4-dihydroisoquinolin-2-ium-2-yl)pyridazin-4-yl)-2,7-diphenyl-9H-fluoren-9-ide;
9-(5-(1-(4-fluorophenethyl)-3,4-dihydroisoquinolin-2-ium-2-yl)-3,6-dimethylpyridazin-4-yl)-2,7-diphenyl-9H-fluoren-9-ide;
9-(5-(1-(4-cyanophenethyl)-3,4-dihydroisoquinolin-2-ium-2-yl)-3,6-dimethylpyridazin-4-yl)-2,7-diphenyl-9H-fluoren-9-ide;
9-(3,6-dimethyl-5-(1-phenethyl-3,4-dihydroisoquinolin-2-ium-2-yl)pyridazin-4-yl)-2,3,6, 7-tetraphenyl-9H-fluoren-9-ide;
9-(3,6-dimethyl-5-(1-(4-methylphenethyl)-3,4-dihydroisoquinolin-2-ium-2-yl)pyridazin-4-yl)-2,3,6,7-tetraphenyl-9H-fluoren-9-ide;
9-(5-(1-(4-fluorophenethyl)-3,4-dihydroisoquinolin-2-ium-2-yl)-3,6-dimethylpyridazin-4-yl)-2,3,6,7-tetraphenyl-9H-fluoren-9-ide; and
9-(5-(1-(4-cyanophenethyl)-3,4-dihydroisoquinolin-2-ium-2-yl)-3,6-dimethylpyridazin-4-yl)-2,3,6,7-tetraphenyl-9H-fluoren-9-ide.

3. The compound of claim 1, wherein said compound is a photochromic compound.

4. The photochromic compound of claim 3, wherein said photochromic compound has an activated absorption maxima of 520-550 nm.

5. The photochromic compound of claim 3, wherein said photochromic compound has two activated absorption maxima of 440-450 nm and 620-750 nm.

6. The photochromic compound of claim 3, wherein the half-life of said photochromic compound is 0-130 ms.

7. The compound of claim 1, wherein the compound having the Formula III is prepared with a method comprising:

(a) reacting a 9-diazofluorene derivative compound having the following Formula V with hex-3-yne-2,5-dione in dry ether in the dark for 24 h to produce a pyrazole compound:

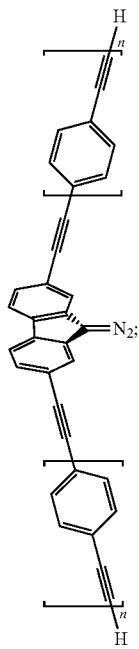

Formula V (b) photolyzing the pyrazole compound having the following formula VI in dry ether for 3 h under a nitrogen atmosphere to produce a diacetyl spirocyclopropene derivative compound:

Formula VI

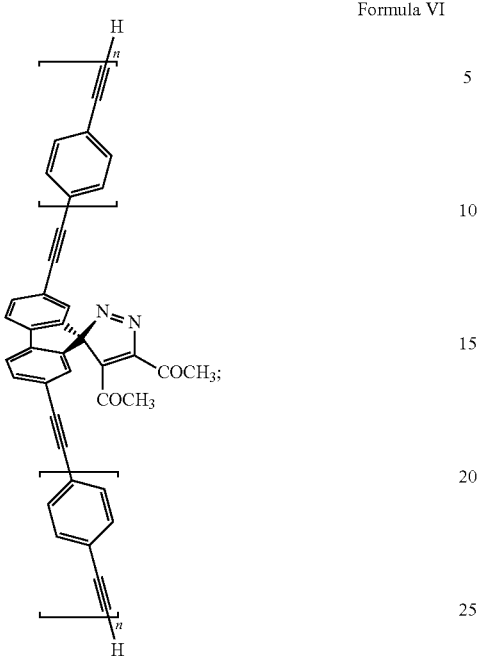

(c) reacting the diacetyl spirocyclopropene compound having the following Formula VII with a substituted 1-aryl-3,4-dihydroisoquinoline compound having the following Formula VIII in dry ether at room temperature under a dry nitrogen atmosphere in the absence of light to produce a THI compound in opened-ring form having the following Formula II:

Formula VII

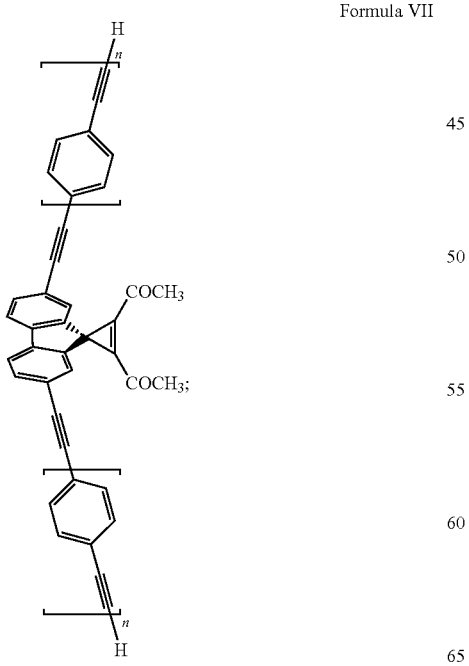

Formula VIII

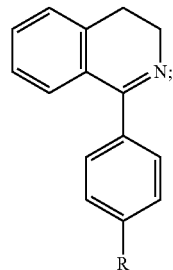

Formula II

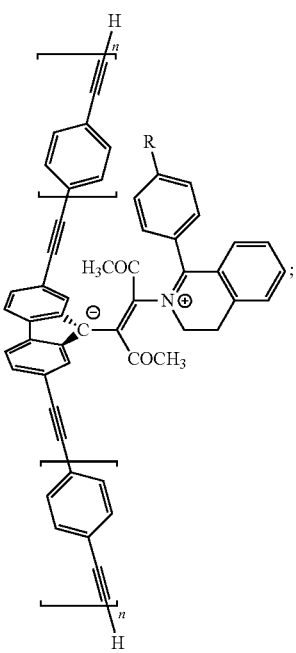

(d) subjecting the THI compound in opened-ring form having the Formula II to a 1,5-electrocyclization reaction to produce a THI compound in closed-ring form having the following Formula I:

Formula I

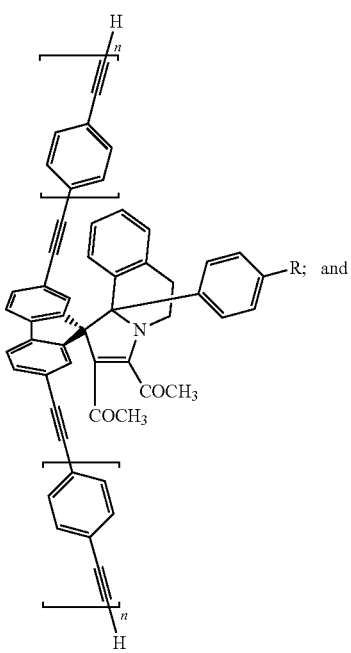

(e) immediately reacting the THI compound in closed-ring form with hydrazine in absolute ethanol at room temperature for 8 h to produce the compound having the Formula III;
wherein:
n is an integer selected from the group consisting of 0, 1, and 2; and
R is selected from the group consisting of hydrogen, alkyl, alkenyl, aryl, arylakyl, acyloxy, heteroaryl, amino, acylamino, alkylamino, acyl, hydroxy, alkoxy, halo, and cyano.

8. The method of claim 7, wherein the THI compound in opened-ring form in (c) is produced via a cyclopropyl-allyl conversion of an intermediate compound having the following Formula IX:

Formula IX

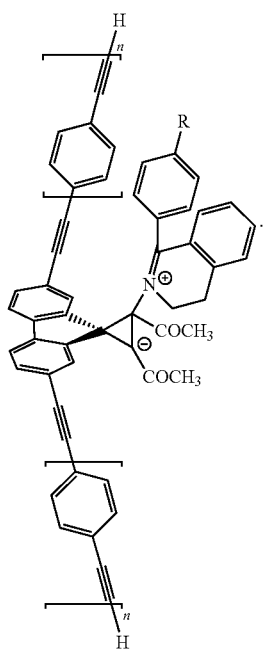

9. The method of claim 7, wherein (d) is a reversible reaction wherein the THI compound in closed-ring form having the Formula I is converted to the THI compound in opened-ring form having the Formula II upon exposure to light.

10. The compound of claim 1, wherein the compound having the Formula III is prepared with a method comprising:

(a) coupling a THI compound having the following Formula X and an alkyne having the following Formula XI in the presence of 5% palladium diphenylphosphinedichloride and CuI/Et$_3$N in dry THF to produce a trimethylsilyl THI compound:

Formula X

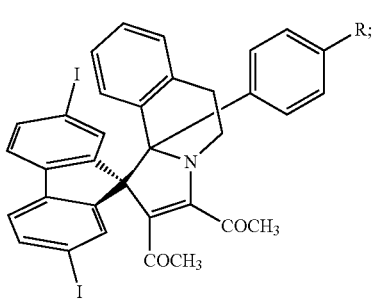

Formula XI

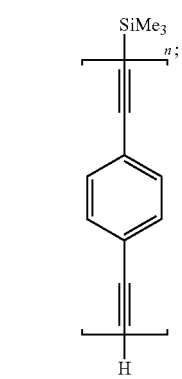

(b) treating the trimethylsilyl THI compound having the following Formula XII with TBAF in dry THF for 12 h to produce a desilylated THI compound:

Formula XII

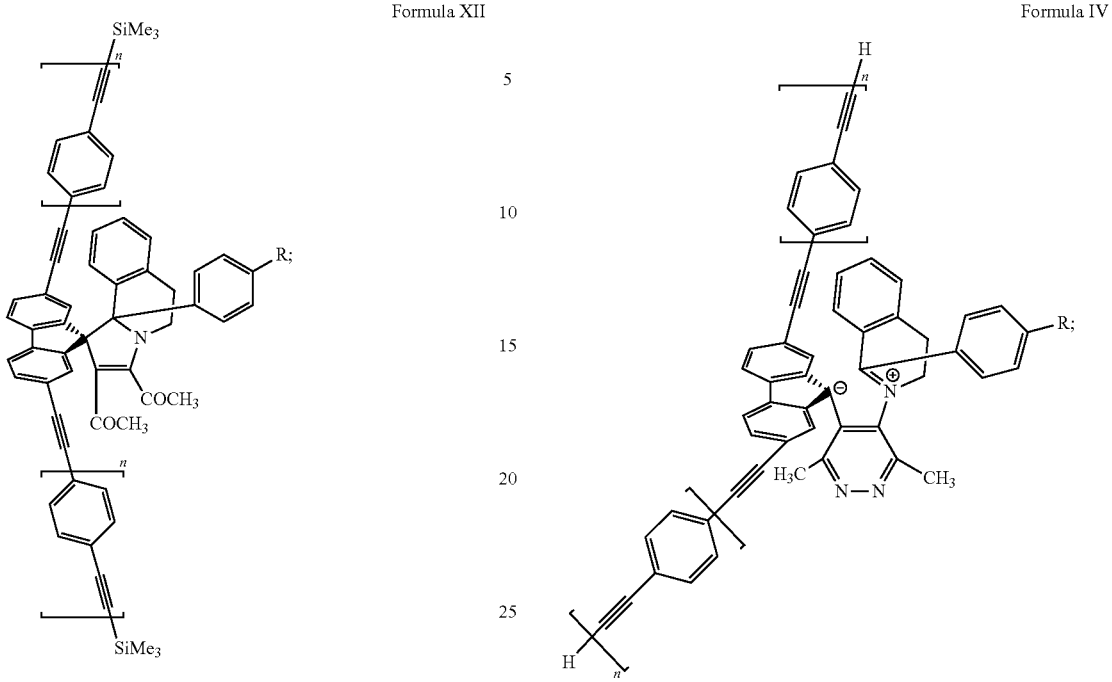

Formula IV (c) immediately treating the desilylated THI compound having the following Formula I with hydrazine hydrate at absolute ethanol at ambient temperature for 8 h to produce a THI in opened-ring form:

Formula I

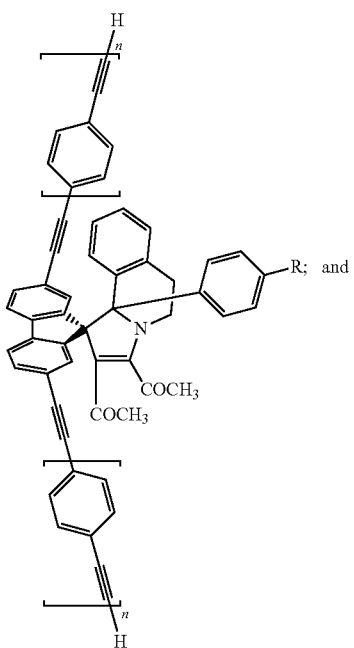

and (d) subjecting the THI compound in opened-ring form having the following Formula IV to a 1,5-electrocyclization reaction to produce the compound having the Formula III:

wherein:

n is an integer selected from the group consisting of 0, 1, and 2; and

R is selected from the group consisting of hydrogen, alkyl, alkenyl, aryl, arylakyl, acyloxy, heteroaryl, amino, acylamino, alkylamino, acyl, hydroxy, alkoxy, halo, and cyano.

11. The method of claim 10, wherein (d) is a reversible reaction wherein the compound having the Formula III is converted into the THI compound in opened-ring form having the Formula IV upon exposure to light.

12. The compound of claim 1, wherein the compound having the Formula III is prepared with a method comprising:

(a) coupling a THI compound having the following Formula X and an alkyne having the following Formula XI in the presence of 5% palladium diphenylphosphinedichloride and CuI/Et$_3$N in dry THF to produce a trimethylsilyl THI compound:

Formula X

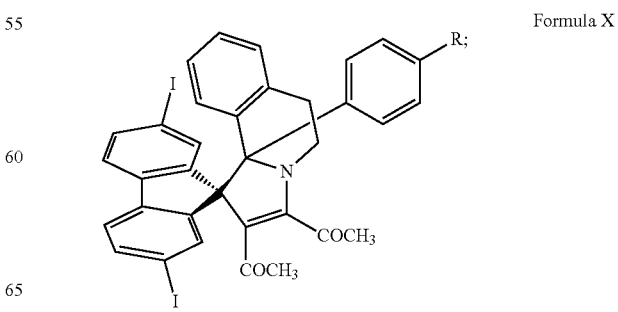

-continued

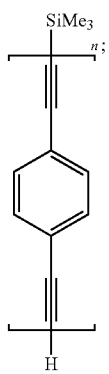

Formula XI (b) treating the trimethylsilyl THI compound having the following Formula XII with TBAF in dry THF for 12 h to produce a desilylated THI compound:

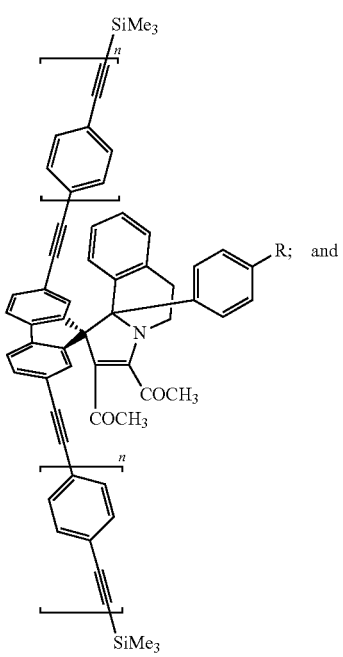

Formula XII (c) immediately treating the desilylated THI compound having the following Formula I with hydrazine hydrate at absolute ethanol at ambient temperature for 8 h to produce the compound having the Formula III;
wherein:
n is an integer selected from the group consisting of 0, 1, and 2; and
R is selected from the group consisting of hydrogen, alkyl, alkenyl, aryl, arylakyl, acyloxy, heteroaryl, amino, acylamino, alkylamino, acyl, hydroxy, alkoxy, halo, and cyano.

13. A photochromic composition comprising:
(a) at least one photochromic compound each having one of the following Formulas I-IV:

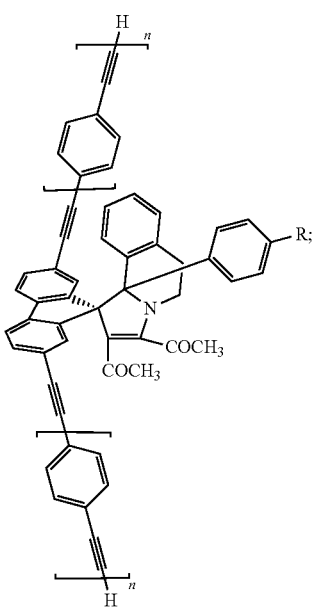

Formula I

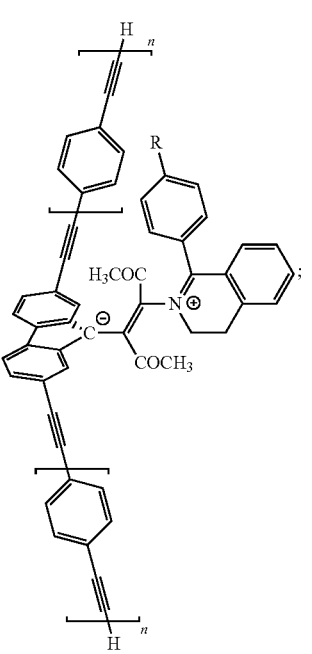

Formula II

Formula III

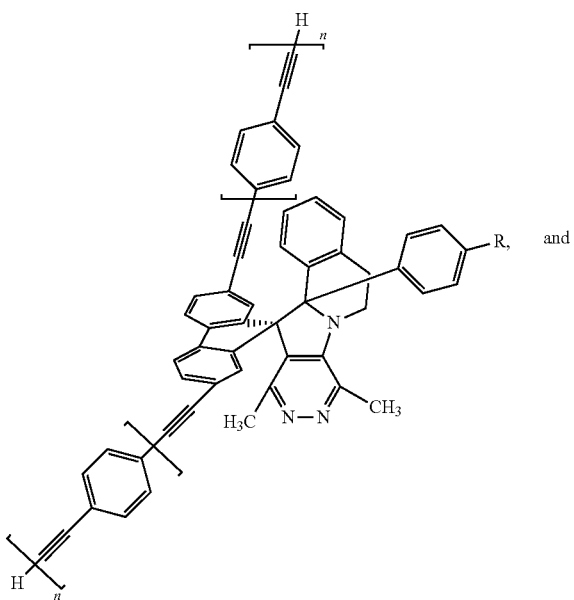

Formula IV

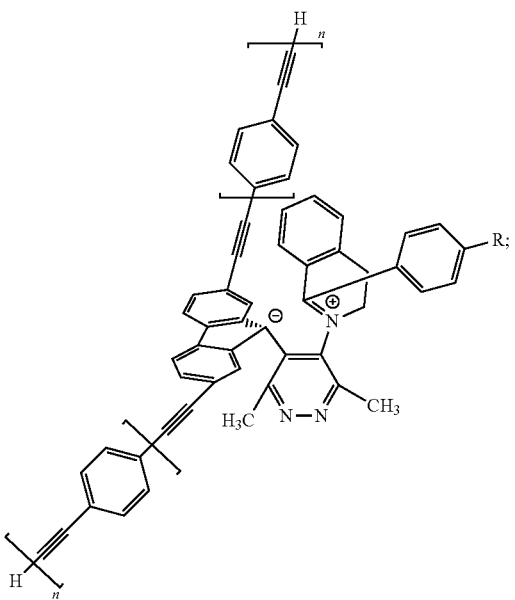

wherein:
n is an integer selected from the group consisting of 0, 1, and 2; and

R is selected from the group consisting of hydrogen, alkyl, alkenyl, aryl, arylakyl, acyloxy, heteroaryl, amino, acylamino, alkylamino, acyl, hydroxy, alkoxy, halo, and cyano;

(b) at least one photochromic compound other than the at least one photochromic compound of (a);
(c) at least one coating;
(d) at least one metal element; and
(e) at least one polymeric organic material;

wherein the at least one photochromic compound of (a) and (b) are chemically bonded to the at least one metal element and the at least one organic material.

14. The photochromic composition of claim 13, wherein the at least one coating is selected from the group consisting of a liquid crystal material, a self-assembling material, polyacrylate, polymethacrylate, poly($C_1$-$C_{12}$ alkyl methacrylate), polyoxy(alkylene methacrylate), poly(alkoxylated phenol methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyester, polyamide, polyimide, polyurethane, poly(urea)urethane, polythiourethane, polythio(urea)urethane, polycyclic alkene, polyurethane, poly(ethylene terephthalate), polyolefin, polystyrene, poly(alpha methylstyrene), copoly(styrene-methylmethacrylate), copoly(styrene acrylonitnile), polyvinylbutyral, and a polymer that is a member of the group consisting of a polyol(allyl carbonate) monomer, a polyfunctional acrylate monomer, a polyfunctional methacrylate monomer, a diethylene glycol dimethacrylate monomer, a diisopropenyl benzene monomer, an alkoxylated polyhydric alcohol acrylate monomer, and a diallylidene pentaerythritol monomer, a copolymer thereof, and a mixture thereof.

15. The photochromic composition of claim 13, wherein the at least one polymeric organic material is selected from the group consisting of a liquid crystal material, a self-assembling material, polyacrylate, polymethacrylate, poly($C_1$-$C_{12}$ alkyl methacrylate), polyoxy(alkylene methacrylate), poly(alkoxylated phenol methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyester, polyamide, polyimide, polyurethane, poly(urea)urethane, polythiourethane, polythio(urea)urethane, polycyclic alkene, polyurethane, poly(ethylene terephthalate), polyolefin, polystyrene, poly(alpha methylstyrene), copoly(styrene-methylmethacrylate), copoly(styrene acrylonitnile), polyvinylbutyral, and a polymer that is a member of the group consisting of a polyol(allyl carbonate) monomer, a polyfunctional acrylate monomer, a polyfunctional methacrylate monomer, a diethylene glycol dimethacrylate monomer, a diisopropenyl benzene monomer, an alkoxylated polyhydric alcohol acrylate monomer, and a diallylidene pentaerythritol monomer, a copolymer thereof, and a mixture thereof.

16. A photoswitch electronic device comprising at least one component connected to a circuit comprising a photochromic composition comprising:

(a) at least one photochromic compound each having one of the following Formulas I-IV:

Formula I

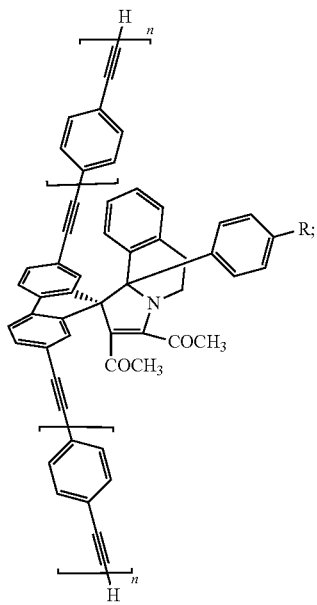

Formula II

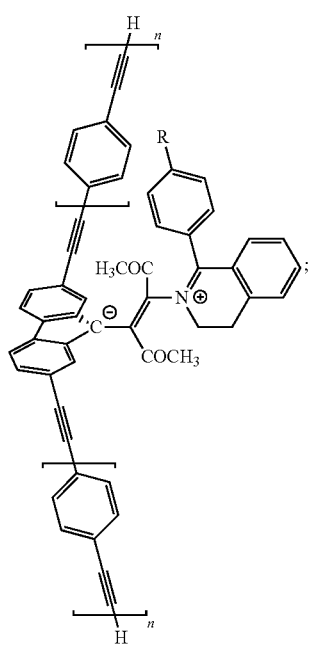

Formula III

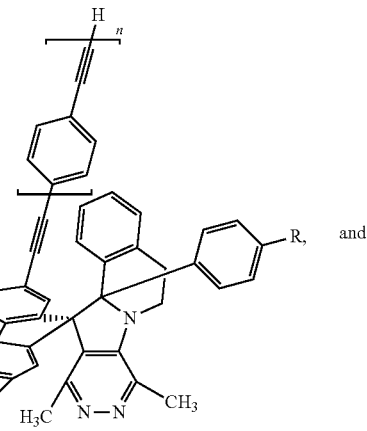

and

Formula IV

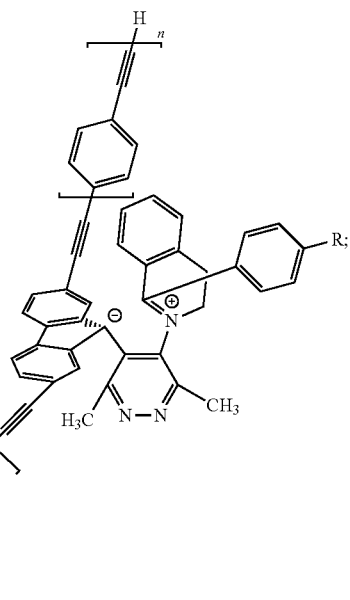

wherein:
n is an integer selected from the group consisting of 0, 1, and 2; and
R is selected from the group consisting of hydrogen, alkyl, alkenyl, aryl, arylakyl, acyloxy, heteroaryl, amino, acylamino, alkylamino, acyl, hydroxy, alkoxy, halo, and cyano;
(b) at least one photochromic compound other than the at least one photochromic compound of (a);
(c) at least one coating;
(d) at least one metal element; and
(e) at least one polymeric organic material;
wherein the at least one photochromic compound of (a) and (b) are chemically bonded to the at least one metal element and the at least one organic material.

17. The photoswitch electronic device of claim 16, wherein the at least one coating is selected from the group consisting of a liquid crystal material, a self-assembling material, polyacrylate, polymethacrylate, poly($C_1$-$C_{12}$ alkyl methacrylate), polyoxy(alkylene methacrylate), poly(alkoxylated phenol methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyester, polyamide, polyimide, polyurethane, poly(urea)urethane, polythiourethane, polythio(urea)urethane, polycyclic alkene, polyurethane, poly(ethylene terephthalate), polyolefin, polystyrene, poly(alpha methylstyrene), copoly(styrene-methylmethacrylate), copoly(styrene acrylonitnile), polyvinylbutyral, and a polymer that is a member of the group consisting of a polyol(allyl carbonate) monomer, a polyfunctional acrylate monomer, a polyfunctional methacrylate monomer, a diethylene glycol dimethacrylate monomer, a diisopropenyl benzene monomer, an alkoxylated polyhydric alcohol acrylate monomer, and a diallylidene pentaerythritol monomer, a copolymer thereof, and a mixture thereof.

18. The photoswitch electronic device of claim 16, wherein the at least one polymeric organic material is selected from the group consisting of a liquid crystal material, a self-assembling material, polyacrylate, polymethacrylate, poly($C_1$-$C_{12}$ alkyl methacrylate), polyoxy(alkylene methacrylate), poly(alkoxylated phenol methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyester, polyamide, polyimide, polyurethane, poly(urea)urethane, polythiourethane, polythio(urea)urethane, polycyclic alkene, polyurethane, poly(ethylene terephthalate), polyolefin, polystyrene, poly(alpha methylstyrene), copoly(styrene-methylmethacrylate), copoly(styrene acrylonitnile), polyvinylbutyral, and a polymer that is a member of the group consisting of a polyol(allyl carbonate) monomer, a polyfunctional acrylate monomer, a polyfunctional methacrylate monomer, a diethylene glycol dimethacrylate monomer, a diisopropenyl benzene monomer, an alkoxylated polyhydric alcohol acrylate monomer, and a diallylidene pentaerythritol monomer, a copolymer thereof, and a mixture thereof.

* * * * *